(12) United States Patent
McKinney et al.

(10) Patent No.: US 10,959,651 B1
(45) Date of Patent: Mar. 30, 2021

(54) HUMAN GAS SENSING GLUCOSE MONITORING AND KETONE FLUCTUATION DETECTION DEVICE

(71) Applicant: Better Life Technologies Group, Inc., San Diego, CA (US)

(72) Inventors: George Anthony McKinney, San Diego, CA (US); Glenn Allan Battle, San Marcos, CA (US); Robert Christopher Walker, Spring Valley, CA (US)

(73) Assignee: BETTER LIFE TECHNOLOGIES GROUP, INC., San Diego, CA (US)

( * ) Notice: Subject to any disclaimer, the term of this patent is extended or adjusted under 35 U.S.C. 154(b) by 890 days.

(21) Appl. No.: 14/933,985

(22) Filed: Nov. 5, 2015

Related U.S. Application Data

(60) Provisional application No. 62/245,151, filed on Oct. 22, 2015, provisional application No. 62/209,037, filed on Aug. 24, 2015.

(51) Int. Cl.
*A61B 5/1455* (2006.01)
*A61B 5/00* (2006.01)

(52) U.S. Cl.
CPC .......... *A61B 5/1455* (2013.01); *A61B 5/0004* (2013.01); *A61B 5/72* (2013.01); *A61B 5/742* (2013.01)

(58) Field of Classification Search
CPC .............. A61B 5/1455; A61B 5/14551; A61B 5/14532; A61B 2562/0233
See application file for complete search history.

(56) References Cited

U.S. PATENT DOCUMENTS

| | | | | |
|---|---|---|---|---|
| 8,855,733 | B2 * | 10/2014 | Hashimoto | A61B 5/1455 600/310 |
| 10,265,006 | B2 * | 4/2019 | Kahlman | A61B 5/14552 |
| 10,307,090 | B2 * | 6/2019 | Rudmann | A61B 5/14552 |
| 2003/0039299 | A1 * | 2/2003 | Horovitz | G01N 27/123 374/141 |

OTHER PUBLICATIONS

Leopold, J.H., et al., Glucose prediction by analysis of exhaled metabolites—a systematic review, BMC Anesthesiology 14:46 (2014).
Palidwar, J., et al., Optical Filters Open Up New Uses for MWIR, LWIR Systems, Photonics Spectra, http://www.photonics.com/Article.aspx?AID=56392 (2014).

* cited by examiner

*Primary Examiner* — Eric F Winakur
(74) *Attorney, Agent, or Firm* — Mu P.C.

(57) ABSTRACT

Devices and methods of detecting gas and volatile organic compounds from skin are disclosed. One system for detecting emissions through skin includes a sensing device having a housing having a top portion and a bottom portion, the bottom portion having a concave-shaped bottom surface creating a cavity region, the at least one light source arranged to emit a spectral range of wavelengths of light into the cavity region, and at least one sensor disposed to receive light emitted by the at least one sensor after the light propagates through at least a portion of the cavity region, the at least one sensor configured to generate a signal based on the received light. The sensing device may also include a communication module configured wirelessly transmit the spectral information to a mobile device for determining a characteristic, for example, a blood glucose level.

18 Claims, 17 Drawing Sheets

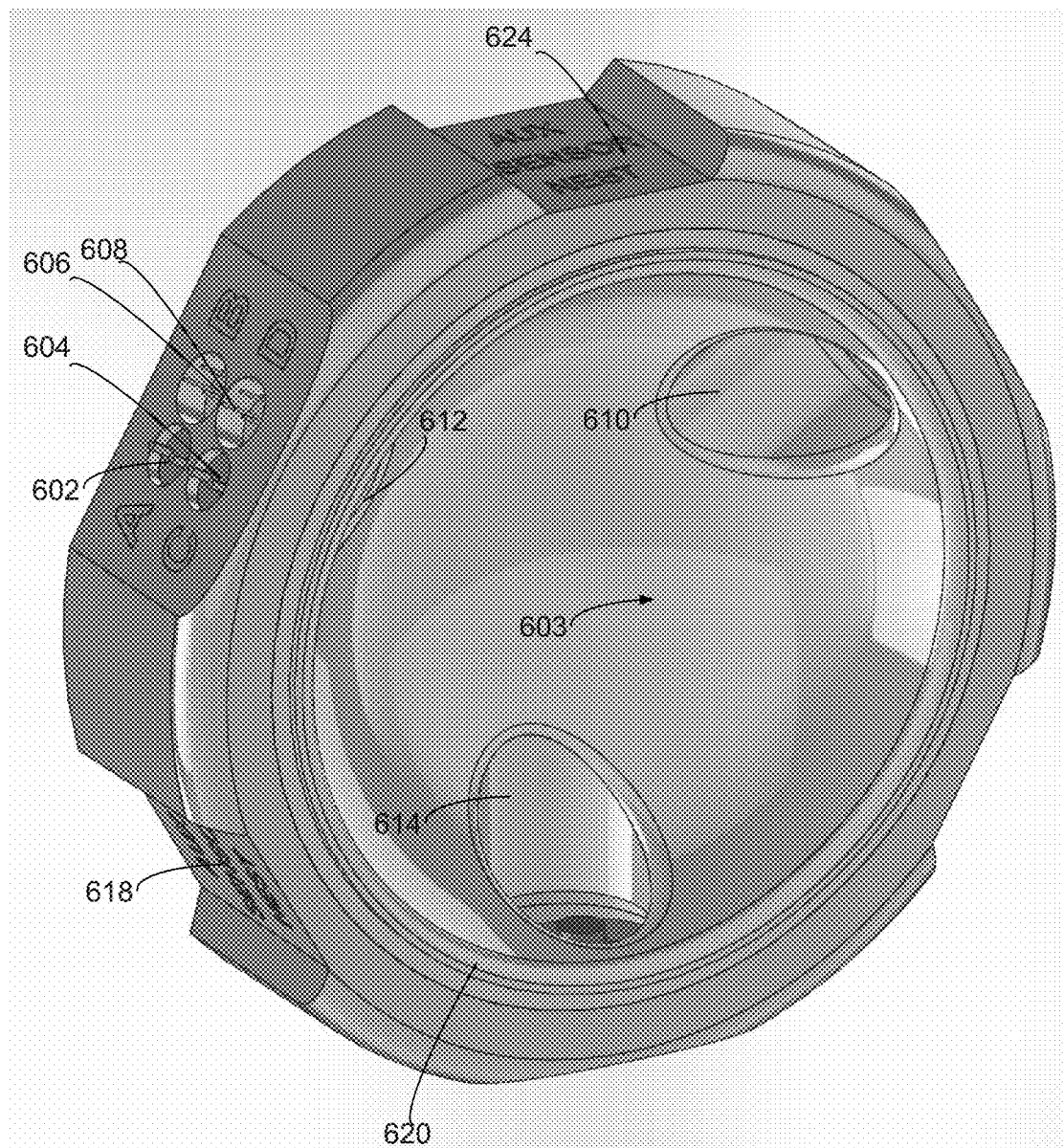

HUMAN GAS SENSING GLUCOSE MONITORING AND KETONE FLUCTUATION DETECTION DEVICE

CROSS REFERENCE TO RELATED APPLICATIONS

This application claims the benefit of U.S. Provisional Application No. 62/245,151, filed Oct. 22, 2015 titled "HUMAN GAS SENSING GLUCOSE MONITORING AND KETONE FLUCTUATION DETECTION DEVICE," this application also claims the benefit of U.S. Provisional Application No. 62/209,037, filed Aug. 24, 2015 titled "HUMAN GAS SENSING GLUCOSE MONITORING AND KETONE FLUCTUATION DETECTION DEVICE," and the disclosures of both of these provisional applications are incorporated by reference herein in their entirety.

FIELD OF THE INVENTION

This disclosure relates to accurately detecting a blood glucose level using a non-invasive technique. And more specifically, to non-invasively determine a blood glucose level based on detecting an indicator emitted from skin.

BACKGROUND

Traditionally methods of blood glucose monitoring employ a blood glucose meter (BGM), an electronic device configured to measure and display a blood glucose level captured on a disposable test strip, and continuous glucose monitoring (CGM), in which glucose levels are determined continuously (generally every few minutes). BGM devices, offer cost advantages, but the information provided by such devices is limited by the frequency at which a user measures their blood glucose level. BGM devices also require a user to obtain blood, typically through the use of a lancet that penetrates a skin surface, which may prove painful and uncomfortable to a user. CGM devices currently on the market are invasive or insufficient in accuracy of measurement. While CGM devices may provide a more accurate depiction of a user's glucose levels than BGM devices, invasive CGM devices may also be uncomfortable and burdensome to a user.

To compensate for these issues, previous non-invasive glucose detection systems have focused on attempting to detect glucose via light radiating through the skin and the measurement of glucose by analyzing a user's breath. Detection of glucose levels by radiating light through the skin can be inaccurate, and such techniques may be made even less effective based on the melanin levels of a user. In other words, the darker the pigmentation the more difficult and inaccurate current devices are. It can also be difficult to detect glucose in breath driven systems due to outer environmental factors and the need for isolating the reading for accuracy, which would require a device to cover the mouth or nose for a 24-hour period, a configuration that carries inherent awkwardness and difficulty.

SUMMARY

The systems, methods and devices of the disclosure each have several innovative aspects, no single one of which is solely responsible for the desirable attributes disclosed herein.

Some implementations of the system and methods disclosed herein are designed to address the problem of determining a blood glucose level using a non-invasive technique. Non-invasive determination of a blood glucose level will obviate the need to draw blood (e.g., prick finger) to determine a blood glucose level, eliminating the pain and mess associated with obtaining a blood sample and also eliminating bio-hazard waste resulting from drawn-blood techniques. Several innovations and aspects of the innovations are described below, however, the described innovations and aspects are not meant to be construed as limiting in any way. In addition, aspects, features and portions of the innovations described in reference to one innovation may be used in another innovation unless otherwise stated.

In one innovation, a system for detecting emissions through skin includes a sensing device having a housing having a top portion and a bottom portion, the bottom portion having a concave-shaped bottom surface creating a cavity region, at least one light source disposed in a portion of the bottom portion, the at least one sensor arranged to emit a spectral range of wavelengths of light into the cavity region, at least one sensor disposed to receive light emitted by the at least one sensor after the light propagates through at least a portion of the cavity region, the at least one sensor configured to generate a signal based on the received light, a processor coupled to the sensor to receive spectral data from the at least one sensor, and determine spectral information based on the received spectral data, the spectral information representative of the spectral data, and a communication module coupled to the processor, the communication module configured to receive the spectral information from the processor and to wirelessly transmit the spectral information. The system can also include a mobile device having a transceiver configured to receive a communication that includes the information representative of the signal, a memory component configured to store data indicative of blood glucose levels corresponding to the spectral information, and a processor coupled to the transceiver and the memory component, the processor configured to receive the spectral information, compare the spectral information to the data indicative of blood glucose levels, and determine a blood glucose level corresponding to the spectral information.

Such systems may include other aspects. The sensing device may further include a display, the processor being further configured to provide information representative of the glucose level on the display. The sensing device further may include a memory component configured to store data indicative of blood glucose levels corresponding to the spectral absorption information, and the processor is configured to compare the spectral information to the data indicative of blood glucose levels and determine a blood glucose level indicative of the spectral information. The sensing device may further include a display, and the processor may be further configured to provide information representative of the glucose level on the display. In one aspect, the processor can be further configured to communicate information representative of the blood glucose level to a remote computer via a network that is at least partially wireless. In one aspect, the sensing device further includes at least one of a heart rate sensor, an oxygen saturation sensor, a temperature sensor, a motion sensor, or an electro cardio signal sensor. In one aspect, the at least one light source includes two or more light sources, and wherein spectral information is based on light received from the two or more light sources. In one aspect, the at least one sensor is configured to generate the spectral information using on IR spectroscopy. In one aspect, the sensing device further includes a Fourier transform infrared spectroscopy (FTIR)

spectrometer, the FTIR spectrometer comprising the at least one light source and the at least one sensor. In one aspect, spectral information received by the processor comprise spectral data over a range of wavelengths, the spectral data representative of how gases in the cavity region absorbs light at each of the wavelengths of light emitted by the at least one infra-red light source.

The sensing device may further include a Michelson interferometer arranged to receive light that propagates from the at least one infra-red light source and transmit beams of light that have different spectrum of wavelengths, where the at least one sensor is arranged to receive light transmitted by the Michelson interferometer that propagates through at least a portion of the cavity region. In one aspect the memory includes predetermined data that includes spectral information and blood glucose levels that correspond to the spectral information.

Another innovation includes a system for detecting emissions through skin, including a sensing device having a collection cavity, a Fourier transform infrared spectroscopy (FTIR) spectrometer arranged to generate spectral data representative of how gas in the collection cavity absorbs infra-red light at a plurality of wavelengths, a processor coupled to the FTIR spectrometer and configured receive the spectral data from the FTIR spectrometer, the processor further configured to generate spectral information based on the spectral data, the spectral information corresponding to a blood glucose level. The sensing device may further include a communication module coupled to the processor, the communication module configured to receive the spectral information from the processor and to wirelessly transmit the spectral information, and the system may further include a mobile device including a transceiver configured to receive a communication that includes the spectral information, a memory component configured to store data indicative of blood glucose levels corresponding to the spectral information, and a processor coupled to the transceiver and the memory component, the processor configured to receive the spectral information, compare the spectral information to the data indicative of blood glucose levels stored in the memory component, and determine a blood glucose level indicative of the spectral information. The sensing device may further include a memory component configured to store data indicative of blood glucose levels corresponding to the spectral information, and wherein the processor is coupled to the memory component, the processor further configured to receive the spectral information, compare the spectral information to the data indicative of blood glucose levels stored in the memory component, and determine a blood glucose level indicative of the spectral information.

Another innovation includes a method of determining a blood glucose level from gas emitted from skin, the method including generating spectral data using a sensor component having at least one light source (for example, an infra-red LED) and at least one sensor, the sensor component disposed in a housing of a sensor device having a cavity region, the sensor component generating spectral data representative of how gas in the cavity region absorbs light; at a plurality of wavelengths, passing through the cavity region, receiving at a processor spectral data from the sensor component, generating, using the processor, spectral information based on the spectral data, the spectral absorption information corresponding to a blood glucose level, and comparing the spectral information to data indicative of blood glucose levels stored in a memory component, and determining a blood glucose level indicative of the spectral absorption information. The method may further include transmitting the spectral information from a sensing device to a mobile device. In one aspect, comparing the spectral information to data indicative of blood glucose levels is performed by a processor coupled to the memory component, the mobile device comprising the processor and the memory component. The method may further include receiving the spectral information on the mobile device, and displaying information representative of the blood glucose level on a display of the mobile device.

BRIEF DESCRIPTION OF THE DRAWINGS

Figure 1:
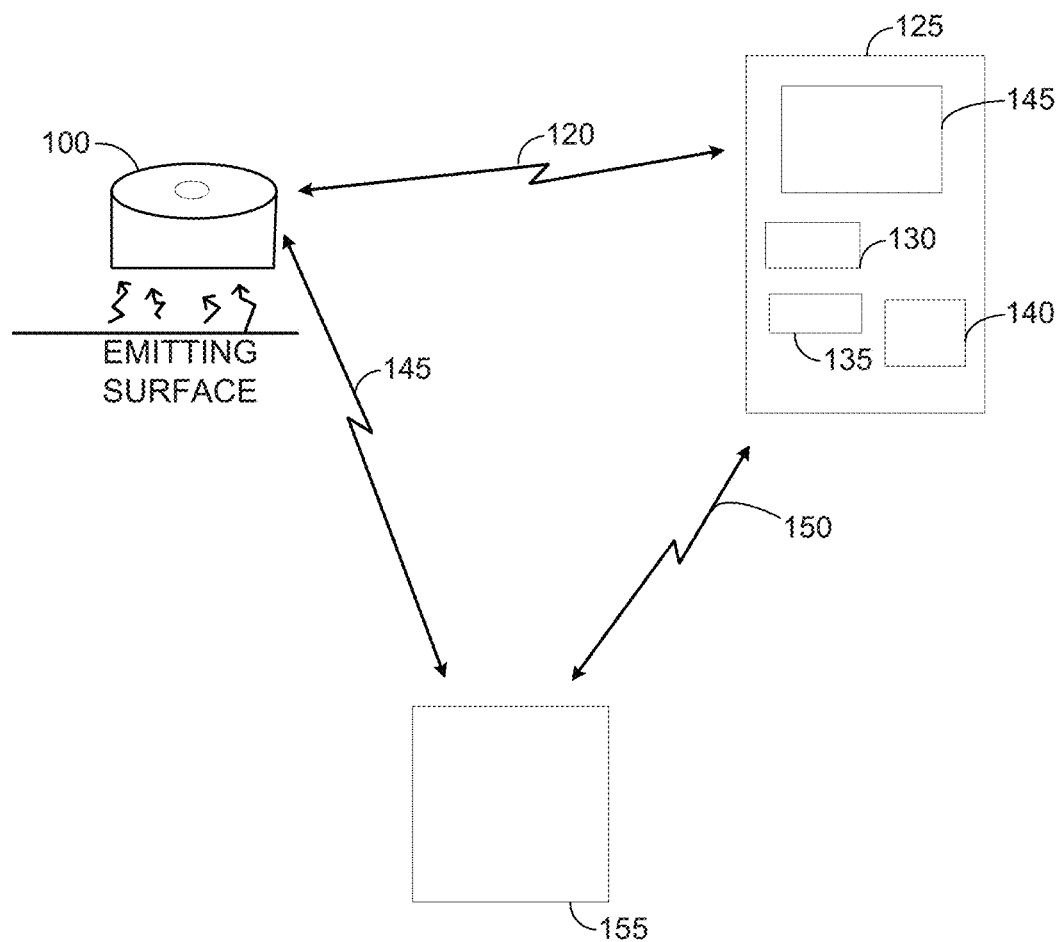

Having thus described certain aspects of the invention in general terms, reference can now be made to the accompanying drawings, which are not necessarily drawn to scale, and wherein:

FIG. 1 is a schematic illustrating examples of a system for detecting and identifying volatile organic compounds (VOC's) or gas emissions, for example, gases of VOC's emitted through skin.

Figure 2A:
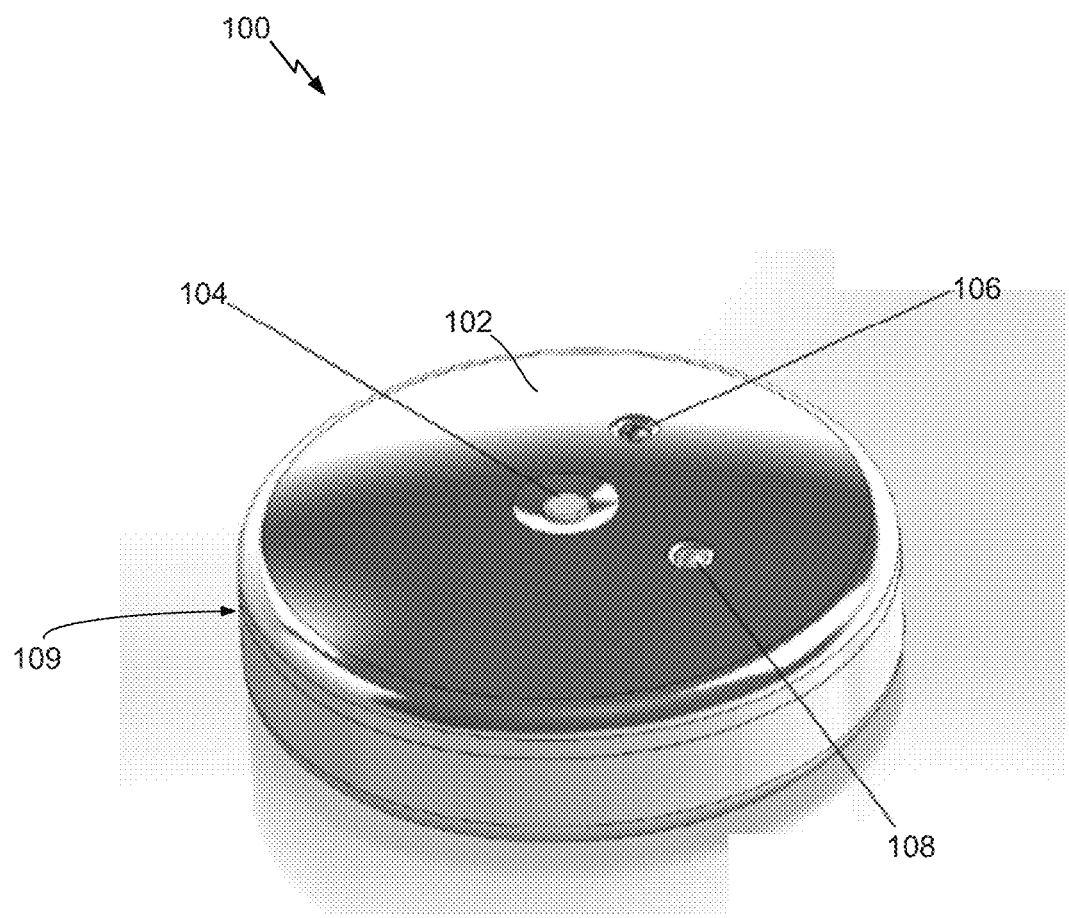

FIG. 2A is a top perspective view illustrating an example embodiment of a sensing device.

Figure 2B:
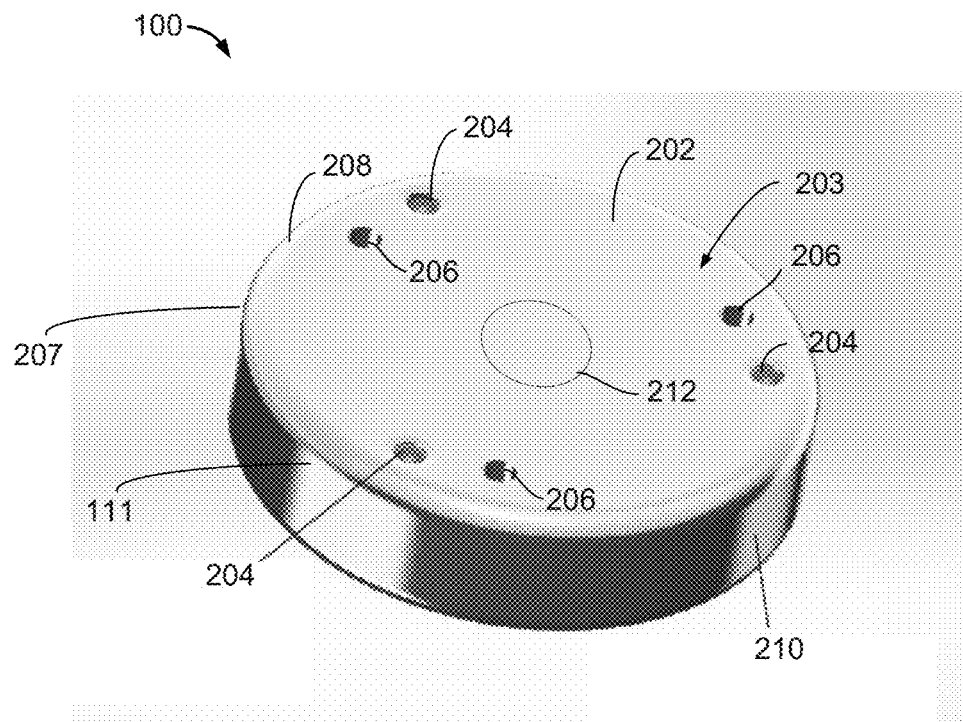

FIG. 2B is a bottom perspective view illustrating an example embodiment of a sensing device.

Figure 2C:
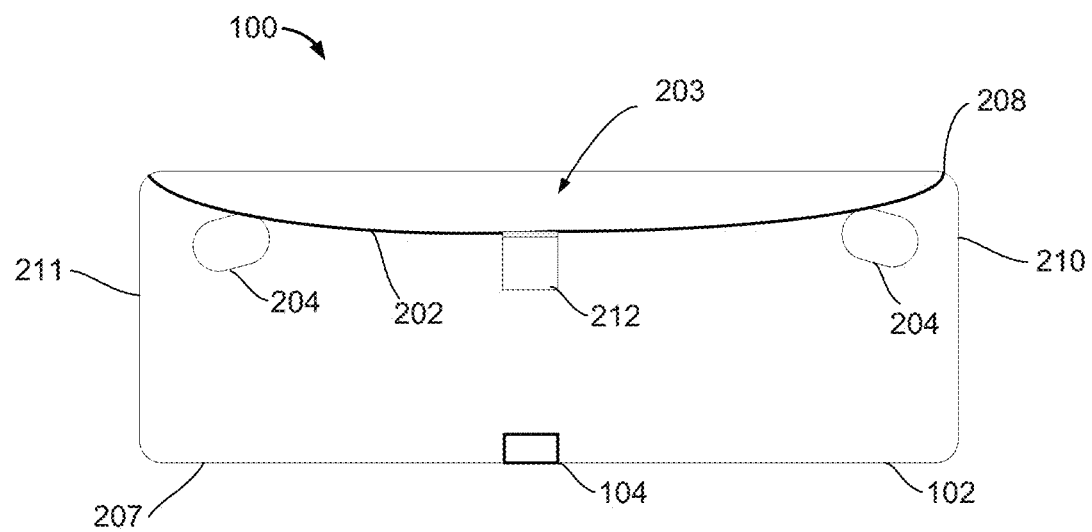

FIG. 2C is a side plan view illustrating an example of an embodiment of a sensing device having a collection cavity in a lower portion of the device that is configured to be placed near or against skin, and examples of an arrangement of light sources and a sensor relative to the collection cavity.

Figure 3A:
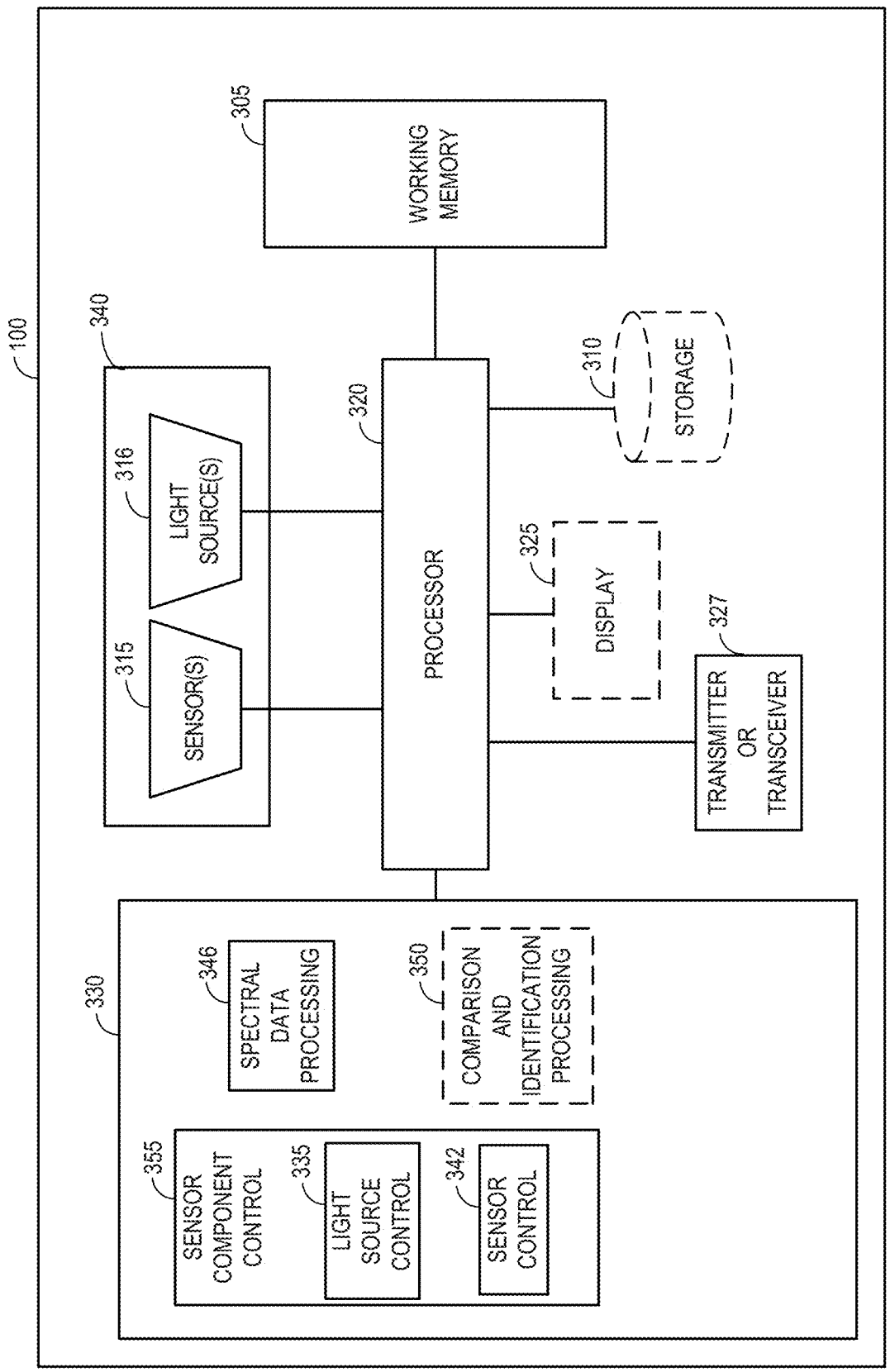

FIG. 3A is a block diagram illustrating an example of an embodiment of components of a sensing device.

Figure 3B:
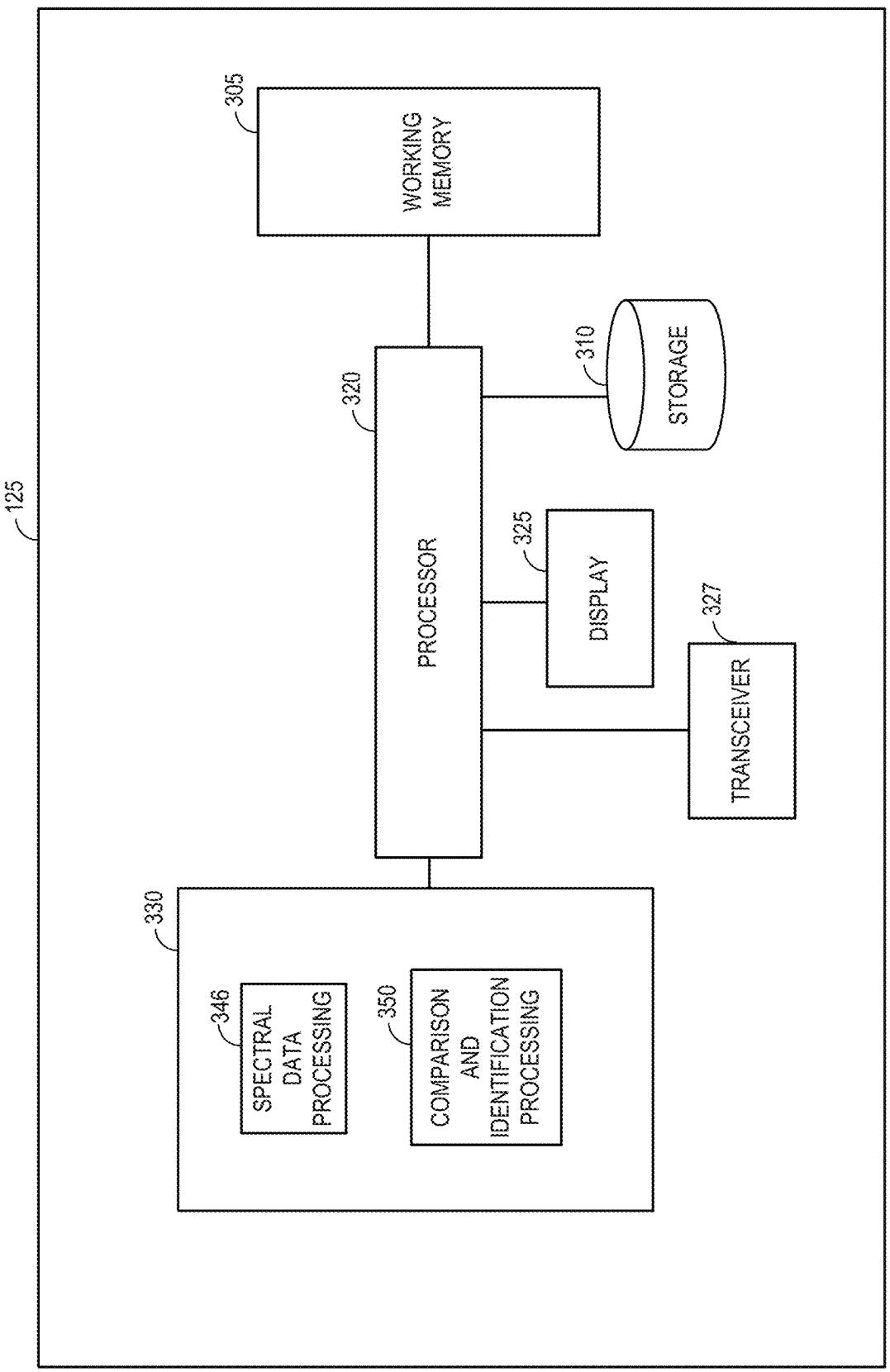

FIG. 3B is a block diagram illustrating an example of an embodiment of components of a mobile device configured to communicate with a sensing device, for example, the sensing device illustrated in FIG. 3A.

Figure 4:
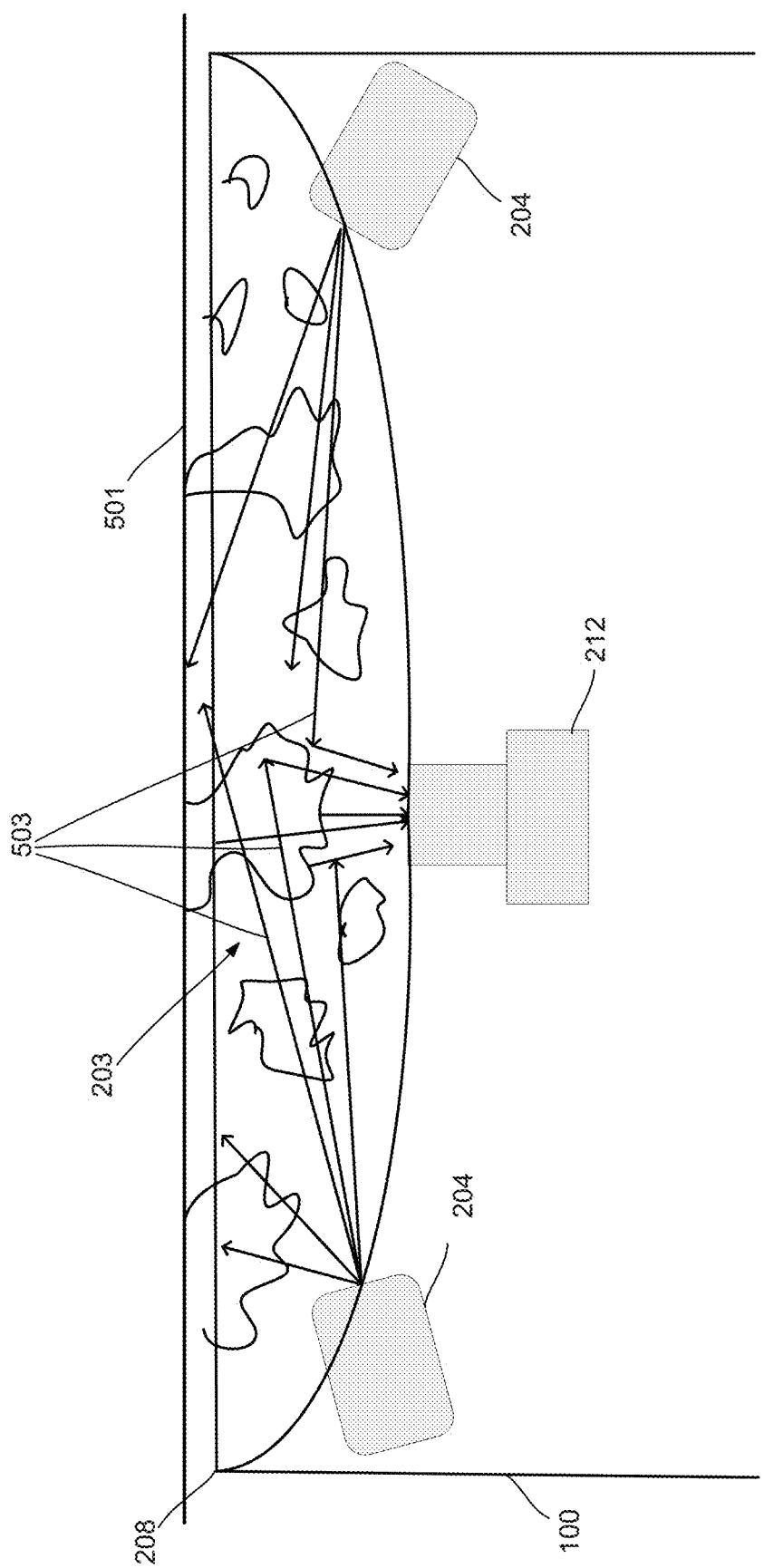

FIG. 4 is a schematic illustrating a representation of at least one light source providing light into a collection cavity of a sensing device, and a sensor detecting radiation from the at least one light source after the radiation emitted from the at least on light source has passed through gases and/or VOC's emitted through or from the skin.

Figure 5A:
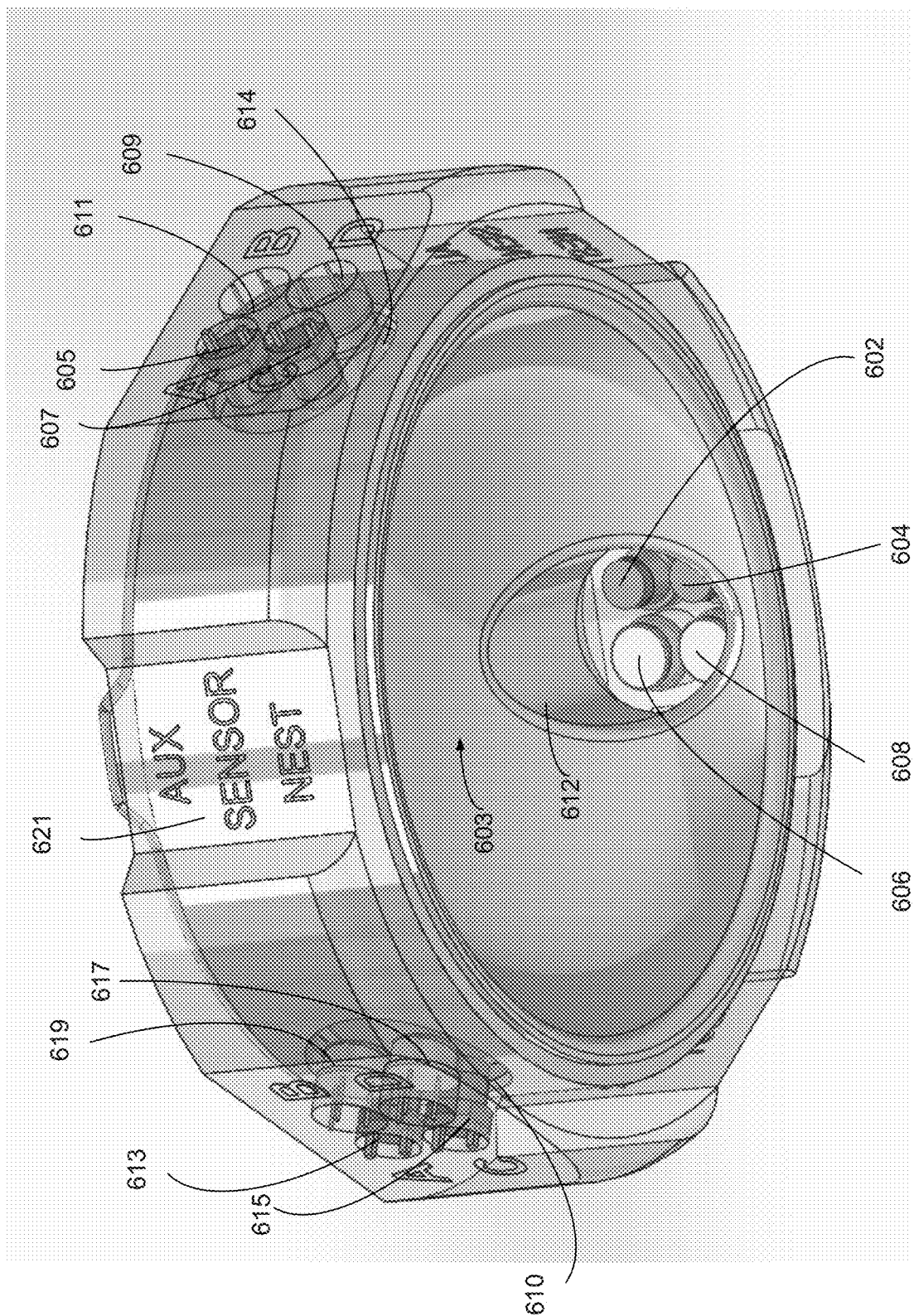

FIGS. 5A and 5B are schematics that illustrate two views of an example of another embodiment of an arrangement of light sources and sensors that may be included in a sensing device 100.

Figure 5C:
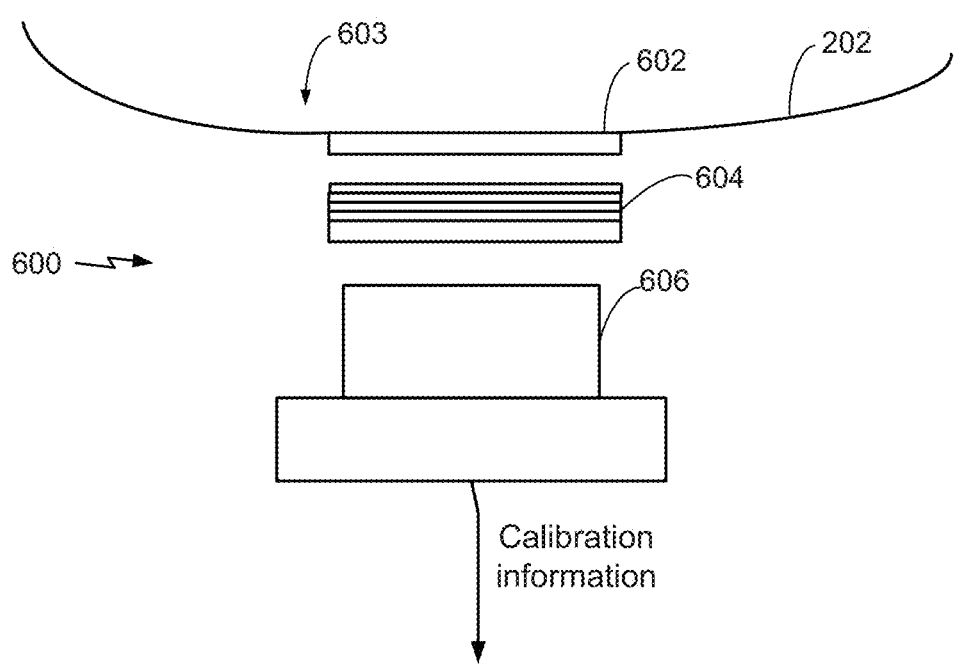

FIG. 5C illustrates an example of an embodiment of a detector that may be used to provide calibration information to the sensing device.

Figure 6:
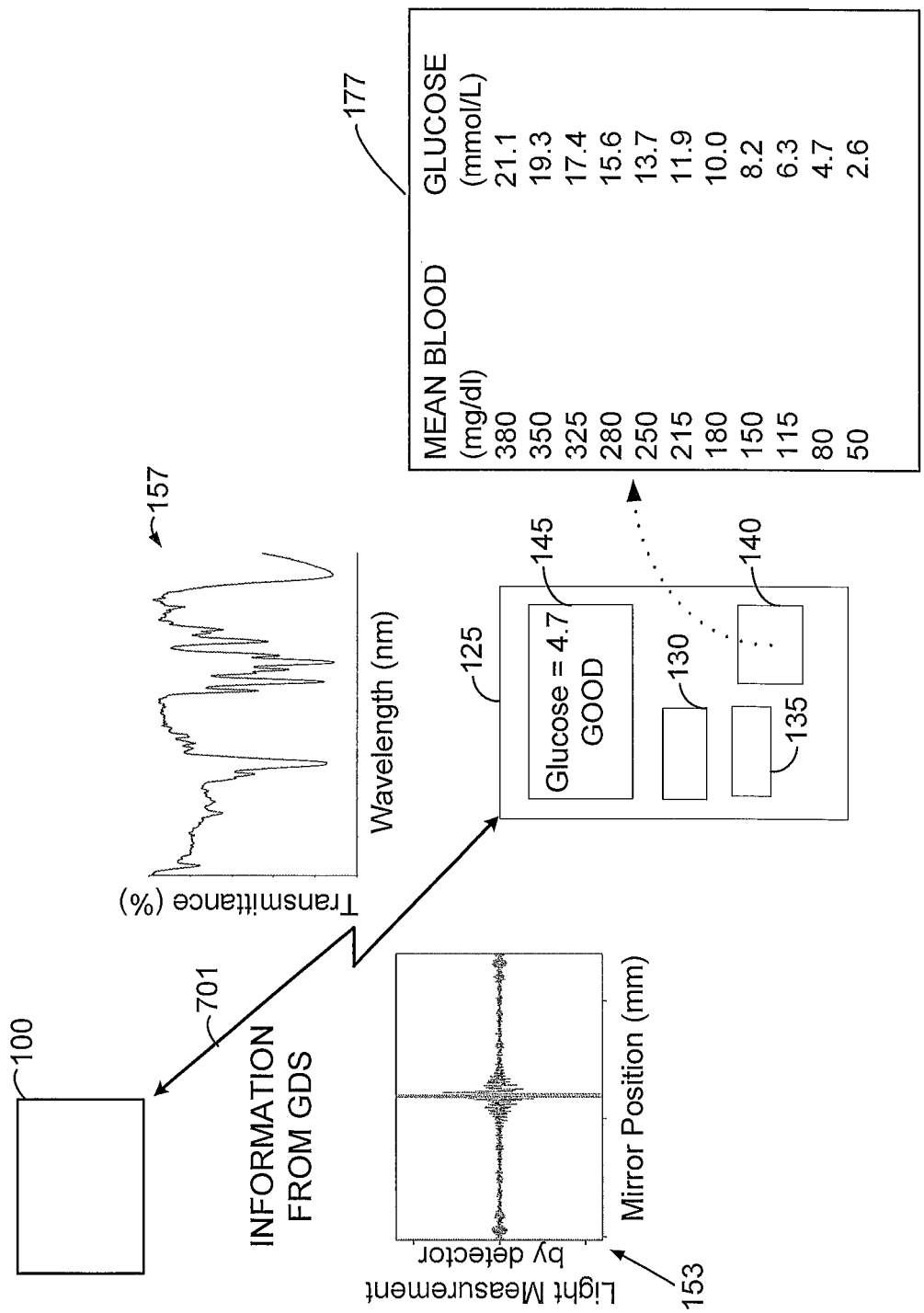

FIG. 6 is a schematic illustrating an example of data/information flow from a sensing device to a mobile device and display of result.

Figure 7:
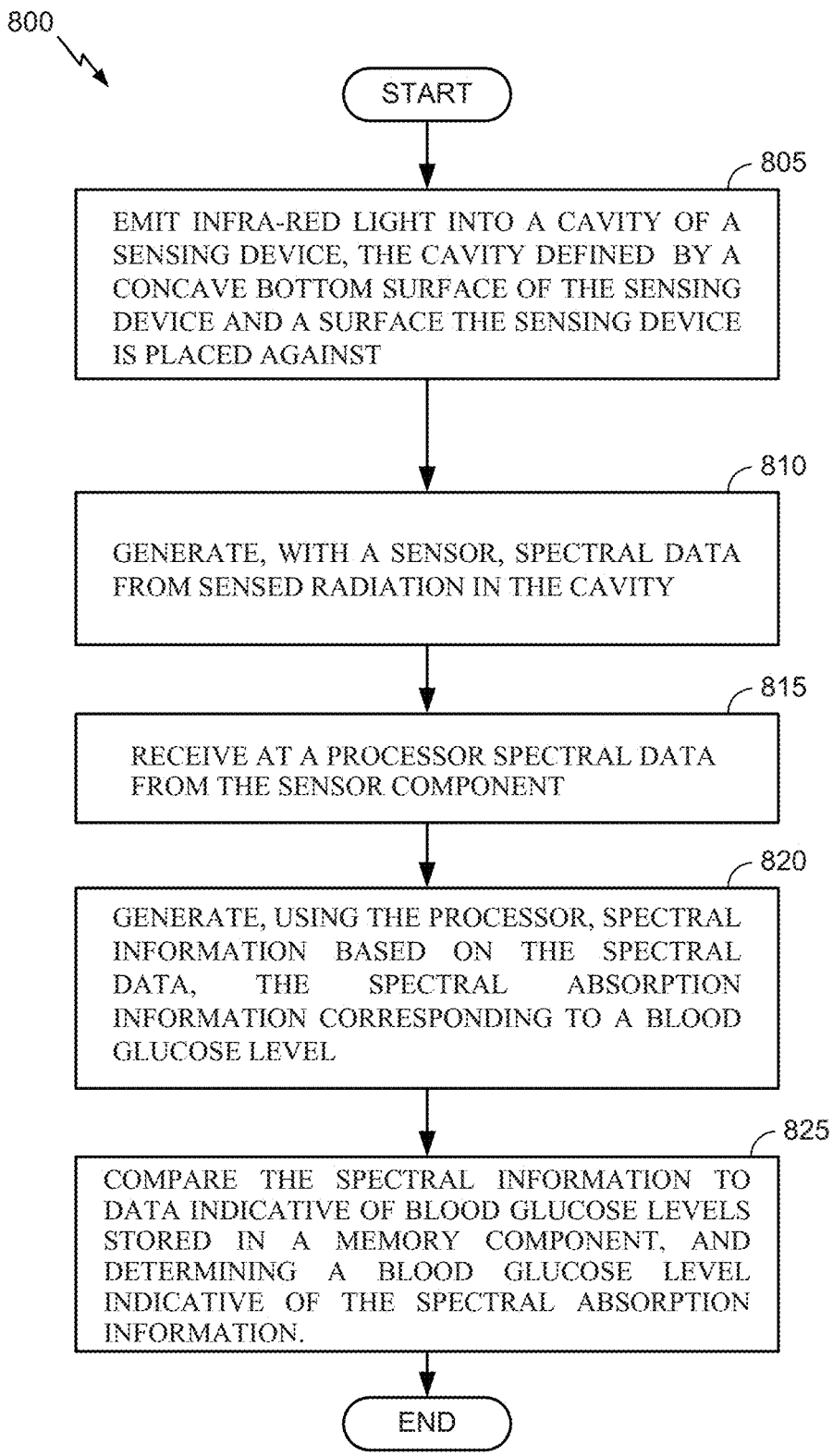

FIG. 7 is flowchart illustrating an example of a method for determining a blood glucose level.

Figure 8:
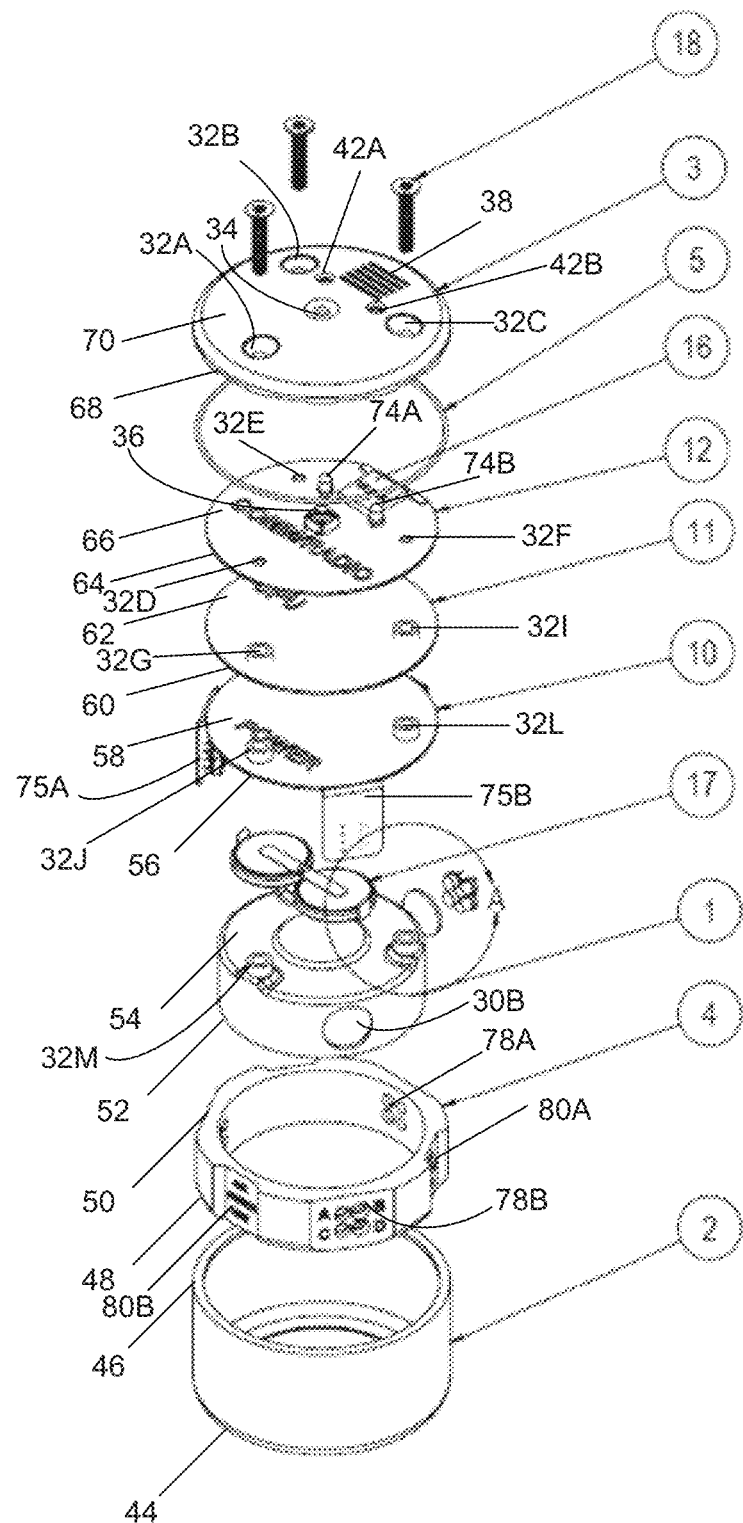

FIG. 8 is an exploded perspective view of an illustrative example of an embodiment of a sensing device.

Figure 9:
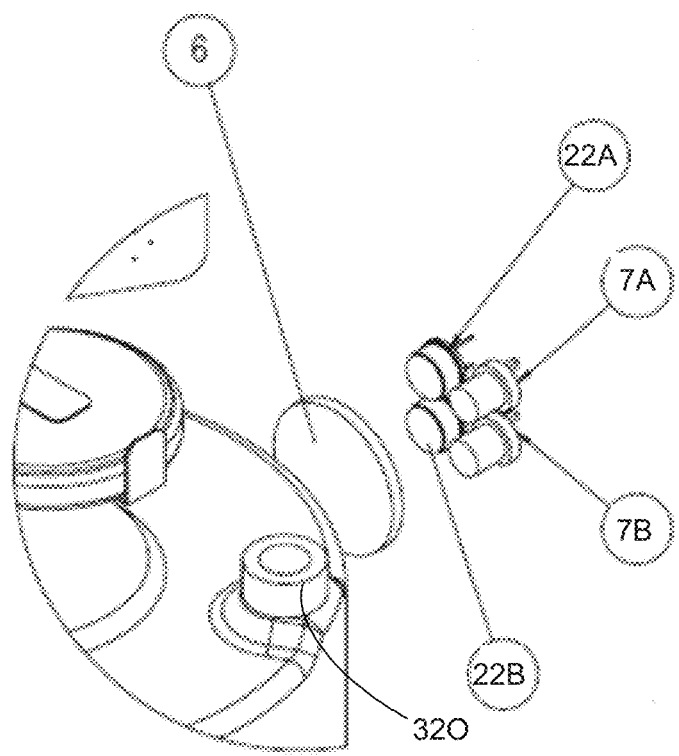

FIG. 9 is a sectional view showing a section of an illustrative example of an embodiment of a sensing device.

Figure 10:
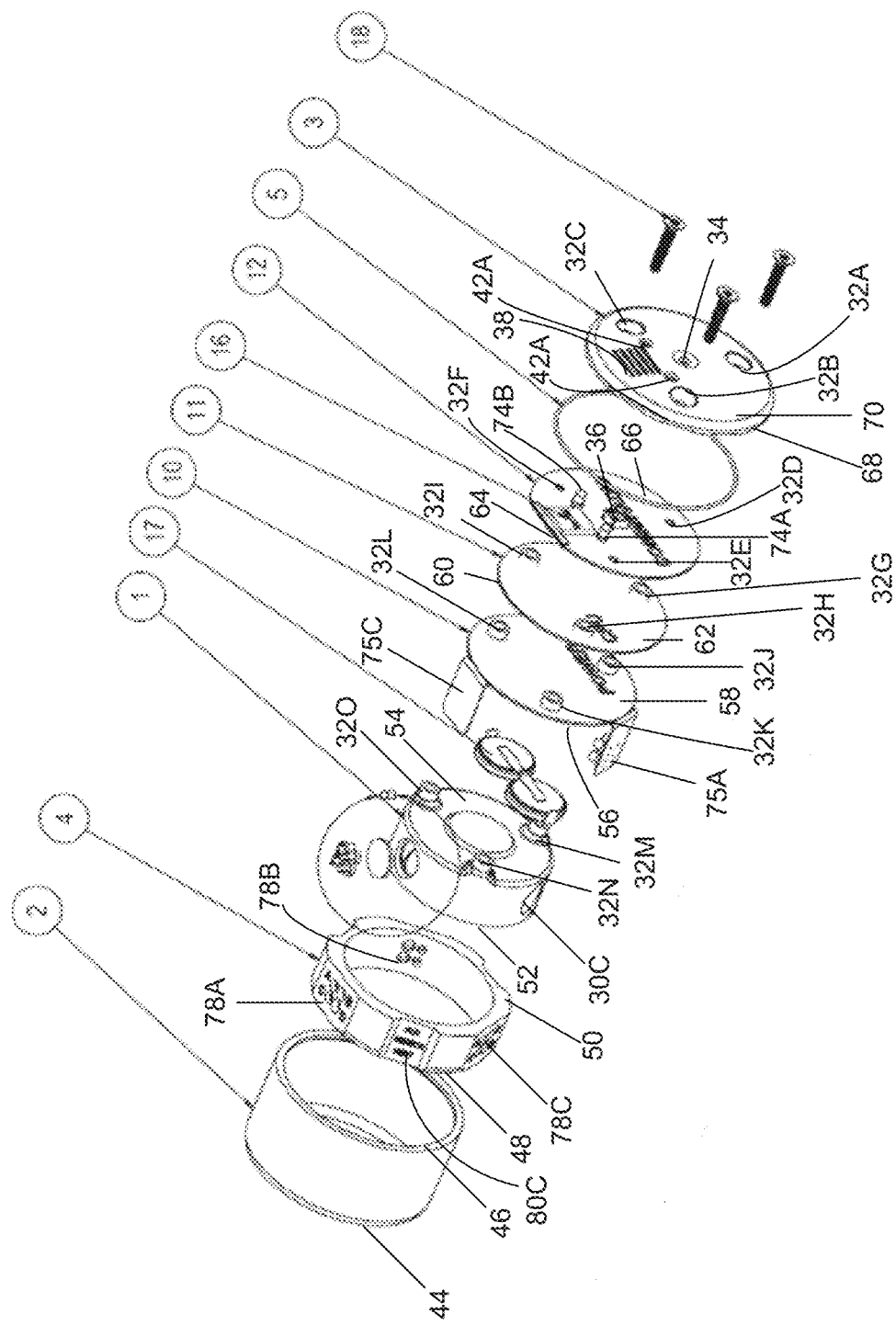

FIG. 10 is an exploded perspective view of an illustrative example of an embodiment of a sensing device.

Figure 11:
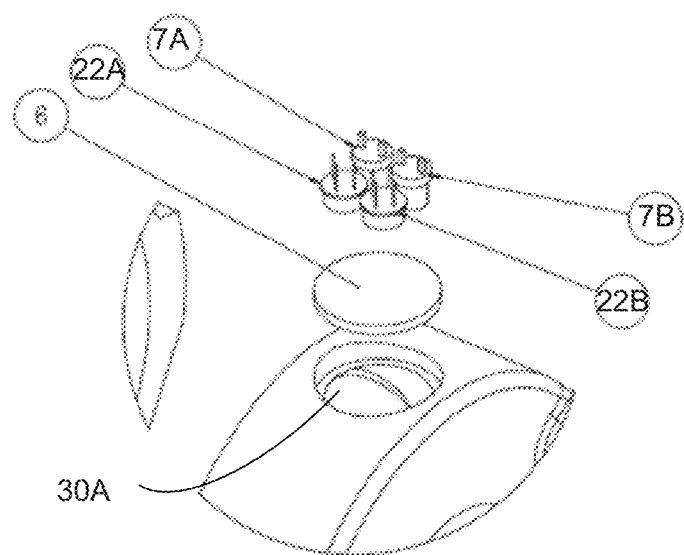

FIG. 11 is a sectional view showing a section of an illustrative example of an embodiment of a sensing device.

Figure 12:
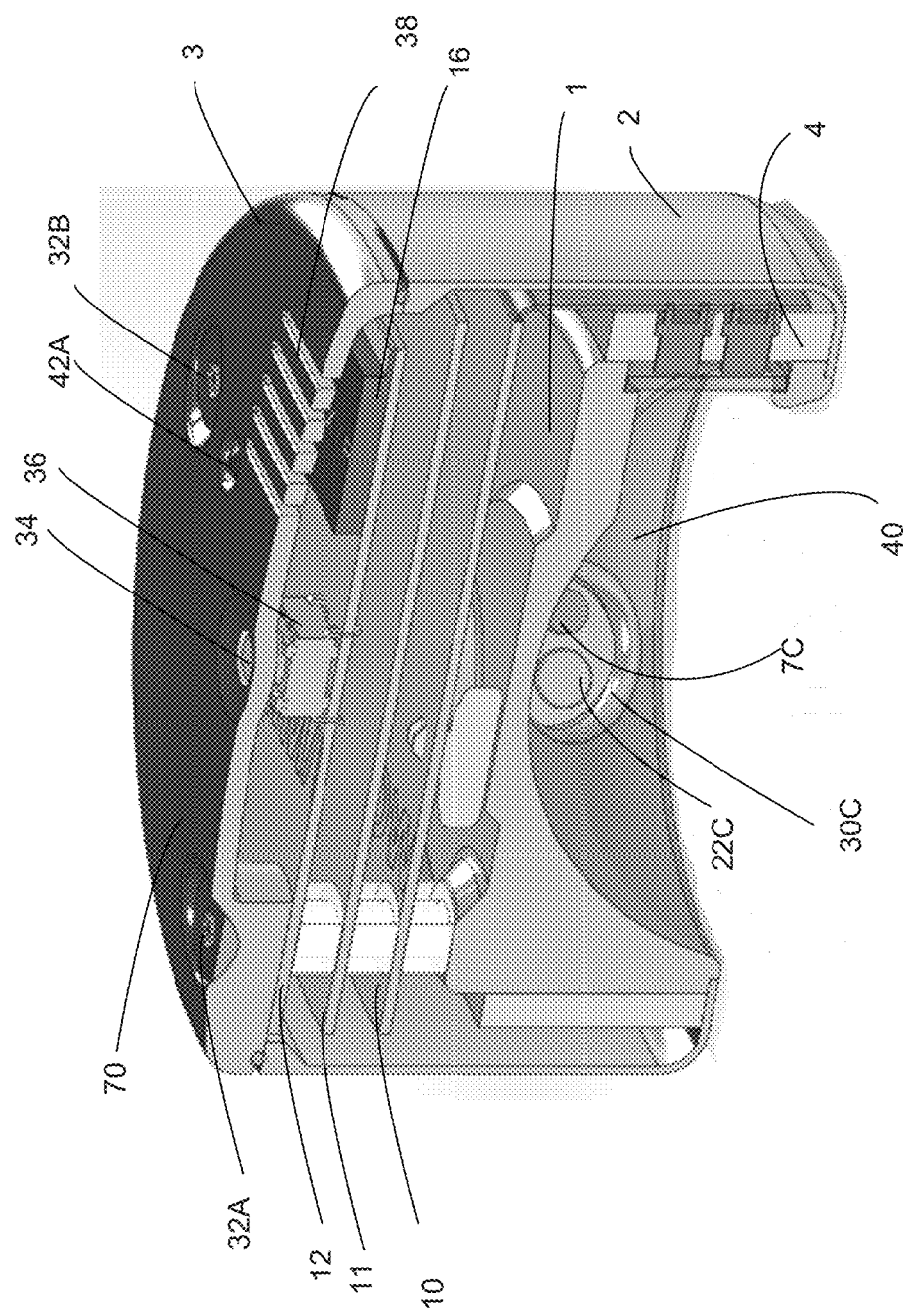

FIG. 12 is a cross-sectional view of an illustrative example of an embodiment of a sensing device.

DETAILED DESCRIPTION OF CERTAIN INVENTIVE ASPECTS

The illustrative examples of embodiments described below allow bypass the barriers of previous non-invasive methods by allowing for the reading of ketone fluctuations as well as continuous glucose readings non-invasively yet accurately and effectively.

Many diabetics suffer additional readable and decipherable diseases that need detection. Embodiments of devices described herein can provide information relevant to a multiplicity of diseases through the accurate detection of bodily functions and continuous glucose and ketone monitoring.

Biomarkers contained in gases and in sweat can give indications about the physical state of the body. Gases emitted from a human body contain bio-signatures which provide insight into the function of human physical systems. Embodiments described herein can detect data from gases and analyze the difference between proper and improper cell function. Embodiments described herein have the ability to read bio-signature data through ketone readings integrated with traditional methods to provide a more accurate measuring system for interpretation in the medical field or to provide a patient with information necessary for self-treatment or management.

One aspect of embodiments described herein is an electrically driven human gas detection and monitoring device that may come in the form of a wristband or attachable disc allowing 24-hour monitoring of glucose levels that bypass barriers inherent with other devices. The detection of human gases represents an elegant solution to the challenges of awkwardness and the constant monitoring of glucose levels which systems created by light and breath systems. Embodiments may further allow for the detection of other biological data of interest in addition to glucose levels.

PDMS photonic biosensor designs can be used for continuous monitoring of glucose concentrations. Micro pulses solid state Lasers for Photonic Biosensors can be Built on a Polymer based Platform (Nano Sensors) Low cost production.

In some embodiments, the sensor technology described herein can provide the capability of reading Ketone fluctuation measurements as well as the ability to track continuous glucose readings (CGR). The sensor may use Infrared (IR) photoacoustic spectroscopy (PAS) to measure glucose by its mid-infrared absorption of light through the skin or by using electromechanically amperometric enzyme electrodes for delectating glucose and other biomarkers. In various embodiments, biomarkers for which information may be detected include, but are not limited to, electrolytes, metabolites, proteins, and amino acids, such as, for example, sodium, chloride, potassium, calcium, lactate, creatine, glucose, uric acid, DHEA, cortisol, interleukins, tumor necrosis factor, and neuropeptides.

Human gases contain bio-signatures which can provide information related to the function of human physical systems. For example, a system in accordance with an illustrative example of one embodiment can read gases and analyze the difference between proper and improper cell function. A system in accordance with an illustrative example of one embodiment may also be configured to read one or more bio-signatures through ketone readings integrated with traditional methods to provide a more accurate measuring system to be interpreted in the medical field or for the patient to respond in a life-affirming manner.

A sensing device in accordance with an illustrative example of an embodiment may include, but are not limited to, one or more of the following features: a top of a bio-sensor, a soft switch on/off button, a multi-colored power indicator (where green indicates the device is in a charged state, red indicates that the device is out of power and yellow indicates the device needs to be charged), a stainless steel surgical seal portion to be placed proximate to or on skin, a bottom of the bio-sensor, a micro-sensor infrared oximeter, one or more key lock screws (to hold the sensor together in a closed configuration) a photo-spectrometer configured to measure gases, nano-optics covering configured to protect the infrared scanner, a micro-sensor body temperature detector configured to detects changes in body temperature, and additional sensors for example, motion sensors (such as an accelerometer/body motion sensor) configured to detect body motion changes related to abnormal functions.

Accurate measurement of bio-signatures may provide data useful for a variety of applications. For example, bio-signature data may provide data indicative of stress, bio-chemical changes, and vitality measurements of athletes. Bio-signature data may also be applicable in drug testing procedures. For example, bio-signature data may provide information related to steroid use, the use of other performance-enhancing drugs, or the use of drugs commonly tested in corporate drug screenings.

Additionally, similar gas detection principles may be applicable in the field of astronomy. Spectrometers are used in many fields. For example, spectrometers are used in astronomy to analyze the radiation from astronomical objects and deduce chemical composition. The spectrometer uses a prism or a grating to spread the light from a distant object into a spectrum. This allows detection of many of the chemical elements by their characteristic spectral fingerprints. If the object is glowing by itself, it will show spectral lines caused by the glowing gas itself. These lines are named for the elements which cause them, such as the hydrogen alpha, beta and gamma lines. Chemical compounds may also be identified by absorption. Typically these are dark bands in specific locations in the spectrum caused by energy being absorbed as light from other objects passes through a gas cloud. Much of our knowledge of the chemical makeup of the universe comes from spectra.

Bio-signature data may also provide information relevant to determining the cause of death in a death investigation. Bio-signature data may also be relevant in security operations by providing indications of drug smuggling, or the presence of explosive devices hidden inhuman orifices. Bio-signature data may also be relevant for measuring an athlete's performance, helping indicate possible areas of improvement in exercise routines. In the medical arena, the detection of gases may provide data currently provided by blood testing, obviating the need to perform blood drawing in some instances.

FIG. 1 is a schematic illustrating examples of a system 1 for detecting and identifying volatile organic compounds (VOC's) or gas emissions, from a surface 103. For example, gases of VOC's emitted by a human, for example, through skin (each and/or all of the VOC's gas emissions and anything else emitted by a human in a gaseous form may be referred to herein as "emissions" for ease of reference, unless explicitly stated otherwise). Various embodiments of such systems are disclosed herein.

In some embodiments, the system 1 includes a sensing device 100 that is configured to sense emissions and generate corresponding spectral data. The sensing device 100 can further be configured to determine a characteristic of a human (from which the emissions were generated), for example, a blood glucose level. Components of the sensing device 100 are further described, for example, in reference to FIG. 3A. The sensing device 100 can use infra-red spectroscopy techniques for sense the emissions. Infrared spectroscopy (IR spectroscopy) is the spectroscopy that deals with the infrared region of the electromagnetic spectrum, that is light with a longer wavelength and lower frequency than visible light. It covers a range of techniques, mostly based on absorption spectroscopy. As with all spectroscopic techniques, it can be used to identify and study chemicals. In some embodiments, radiation other than IR is used with spectroscopy techniques to generate the spectral data. In some embodiments, the Near Infrared (NIR) and Mid Infrared spectrum is used to detect specific gases and their spectral signatures. In some embodiments, the diffusion, reflectivity and gas density spectral values that relate to blood glucose can be determined using a thin-film coated optic as a fixed base line that mimics a normal spectral signature of glucose.

In another embodiment, the system 1 includes a sensing device 100 and further includes a mobile device 125, which is in communication with the sensing device 100 via communication channel 120. In various embodiments the communication channel 120 allows for communication via a wireless protocol (e.g., Bluetooth) or a wired protocol (e.g., USB interface). The sensing device 100 is configured to sense emissions and generate corresponding spectral data, and is also configured to transmit spectral information to the mobile device 125, the spectral information being representative of the spectral data corresponding to the sensed emissions. For example, the spectral data detected may include the strength of a signal sensed at a plurality of wavelengths in a range or wavelengths. In this embodiment, the mobile device 125 includes a transceiver 130, a processor 135, and a memory component 140. The mobile device 125 is configured to determine a characteristic of the human from which the emissions were generated, for example, a blood glucose level. This may be done, for example, by receiving the spectral information (or e.g., spectral data, or any information representative of the sensed emissions), further processing the spectral information to determine a level of a sensed characteristic, and then comparing the spectral information (or information based on the spectral information) to human characteristic information stored in the memory component (e.g., blood glucose levels), and determining characteristic information that corresponds to the level of the sensed characteristic (and the spectral information). For example, the mobile device 125 can receive spectral information representative of the sensed emissions, which may be a detected signal strength across a plurality of wavelengths in a range of wavelengths, such spectral information sometimes being referred to as a spectral signature. Then, knowing the spectral signature of glucose (for example, an infra-red spectral signature), the spectral information can be processed to determine if glucose is present and at what levels, and to determine a value indicative of the level of glucose present (for example, in mg/dl) based on the sensed emissions. Then, by comparing the value indicative of the level of glucose to data stored in memory, the blood glucose level in mmol/L can be determined. In other words, determining the human characteristic information that corresponds to emissions sensed by the sensing device 100. In some embodiments, mobile device 125 may also include a display 145 coupled to the processor 135, and information received from the sensing device 100, information generated by processor 135 and/or information relating to a determined human characteristic may be communicated to be shown on the display 145 by the processor 135. Such processing can also be performed on the sensing device 100 if suitably configured, and in such implementations the mobile device may also include a display to show results of sensed emissions. Certain components of the mobile device 125 are further discussed herein, for example, in reference to FIG. 3B.

In another embodiment, the system 1 may further include another computing device 155, which may be, for example, another mobile computer (e.g., a cell phone, or a laptop tablet), a desktop computer or a server (or server system). The computing device 155 may be configured to communicate with the sensing device 100 via a (wired or wireless) communication channel 145, the mobile device 125 via a (wired or wireless) communication channel 150, or both. In various embodiments, the computing device 155 may be configured to send information to the sensing device 100 and/or the mobile device 125 that is stored on the sensing device 100 and/or mobile device 125 and used to determine a human characteristic that corresponds to the sensed emissions. For example, the computing device 155 may send information that is used that is compared to data generated based on the sensed emissions. Also, the computing device 155 may send information that is used to determine "signatures" of the sensed emissions or be used during processing of the sensed data to generate information related to the sensed emissions that is compared to pre-stored information of human characteristics. For example, the sent information may include algorithm information, or information for calibrating a sensor or light source of the sensing device, or information that is used to control a sensor or a light source of the sensing device 100 (for example, light source modulation information that is used to produce desired emitted wavelengths of light across a range of wavelengths. In some embodiments, information may be transmitted by the mobile device 125 or the sensing device 100 to the computing device for storage, further processing or further communication to another device.

In some embodiments, the mobile device 125 and/or computing device 155 may include a user interface. The user interface may allow for the selection of data, such as, for example, to select between data received from multiple sensing devices 100 or stored data. The interface may also allow a user to access, view, and print stored data. The user interface may also allow a user to select instructions to be sent to a sensing device 100. In some embodiments, the user interface includes a touch screen interface.

In some embodiments, the system 1 may further include an insulin delivery device such as an insulin injection device, an insulin pump, an insulin patch, or an insulin patch injector. In such embodiments one or more of the sensing device 100, the mobile device 125, and the computing device 155 may communicate with the insulin delivery device to provide data relevant to time and amount of insulin dosage. The insulin delivery device may provide delivery data to one or more of the sensing device 100, the mobile device 125, and the computing device 155. In an illustrative example one or more of the sensing device 100, the mobile device 125, and the computing device 155 may determine a dosage and a time of dosage and may communicate the dosage and time of dosage to the insulin delivery device. The insulin delivery device may supply the determined dosage in accordance with the data received.

FIG. 2A is a top perspective view illustrating an example embodiment of a sensing device 100. An example of an upper portion 109 of the sensing device 100 is illustrated in FIG. 2A. In this embodiment, the sensing device 100 may include a top surface 102 and a "power" button 104 to turn the sensing device 100 on and off disposed in the top surface 102. The sensing device 100 may also include a power LED 108 disposed in the top surface such that light from the power LED 108 is visible when the top surface 102 is visible, the sensing device 100 further including a control to activate the power LED 108 when the sensing device 100 is on. The sensing device 100 may also include a Bluetooth LED 106 disposed in the top surface such that light from the Bluetooth LED 106 is visible when the top surface 102 is visible. The sensing device 100 further includes a control (not shown) to turn on the Bluetooth LED when Bluetooth wireless protocol is being used.

FIG. 2B is a bottom perspective view illustrating an example of one embodiment of a sensing device 100, for example, the sensing device 100 illustrated in FIG. 1. The sensing device 100 includes a lower portion 211, which generally refers to a lower or bottom section of the sensing device 100. The sensing device 100 includes a concave bottom surface 202 and an edge 208 along the perimeter of the bottom surface 202. The concave bottom surface 202 forms a cavity 203 on the bottom of the sensing device 100. The edge 208 and the bottom surface 202 are configured such that when the edge 208 is placed against a surface (for example, a skin surface), a chamber or cavity is defined between the bottom surface 208 and the surface that the sensing device 100 is placed against. The sensing device also includes a side 210, which in this embodiment is cylindrical-shaped. The side 210, bottom surface 202, and the top surface 102 define an embodiment of a housing 207 of the sensing device 100.

The sensing device 100 also includes at least one light source (or light emitter) 204 arranged to emit light into the cavity defined by the bottom surface 202. As illustrated, this embodiment includes three light sources 204. Other embodiments may include two light sources, or more than three light sources. In this embodiment, the light sources 204 are infra-red LEDs. In this embodiment the light sources 204 are the same, that is, emit a similar (or identical) spectrum of light. Other embodiments may include multiple light sources where at least one of the light sources is different from the other light sources. Different light sources may be used to emit a desired spectrum of wavelengths that a single light source may not be able to produce, and thus provide the functionality to detect a larger number of gases or VOC's within the cavity 203.

The sensing device 100 may also include fasteners 206, for example screws or other connecting hardware which hold the structure of the sensing device 100 together or components in place within the sensing device 100.

The sensing device 100 may also include a detector 212, which is disposed within the housing 207 and proximate to the bottom surface 202 such that the detector 212 can receive light which is emitted by the at least one light source 204 after the emitted light propagates through at least a portion of the cavity 203 and through emissions in the cavity 203. Although the detector 212 is illustrated in the center of the bottom surface 202 in this embodiment, the detector 212 may be disposed in other positions in other embodiments, where the detector 212 will still detect/receive radiation from the cavity 203. In this embodiment, the detector 212 includes a optic disposed in the bottom surface 202 (for example, a sapphire optical element) which allows radiation in the cavity 203 to propagate to a sensing component of the detector 212, the sensing component disposed in the housing 207 such that the optic is between the sensing component and the cavity 203.

FIG. 2C is a side plan view illustrating an example of an embodiment of a sensing device 100, for example the sensing device 100 illustrated in FIGS. 2A and 2B, having a collection cavity in a lower portion of the device that is configured to be placed near or against skin, and examples of an arrangement of light sources and a sensor relative to the collection cavity. Only some of the components of the sensing device 100 are shown for clarity of the drawing. An arrangement of the housing 207, side 210, top surface 102, power bottom 104, surface 202 and bottom edge 208 of the sensing device 100 are illustrated. FIG. 2C illustrates one configuration of the bottom surface 202, forming a single cavity 203. In other embodiments, a bottom surface 203 can be structured to from two of more cavities, where each cavity includes at least one light source and at least one detector. FIG. 2C also illustrates that the light sources 204 may be positioned at an angle with respect to the lower edge 208 to provide light into the cavity 203 in the direction of the detector 212.

FIG. 3A is a block diagram illustrating an example of an embodiment of components of a sensing device 100. In this example, the sensing device 100 includes a processor 320 coupled to a sensor component 340, which includes a least one sensor 315 and at least one light source 316. In some embodiments, the sensor component 340 may be a Fourier transform infrared spectroscopy (FTIR) spectrometer. In some embodiments, a light source 316 may be an infra-red LED or an infra-red solid state device. When there are multiple light sources 316, the light sources may be the same or different. That is, emit different spectrums of radiation that include different wavelengths, emit radiation in a spectrum that is centered at a different frequency, emit a narrower or broader range of wavelengths. A sensor 315 can be a sensor that is suitable to collect radiation of a desired wavelength, for example, infra-red light. The sensor(s) 315 may be tunable to detect radiation at selected wavelengths, and be controllable to scan a series or range of wavelengths to detect radiation having such wavelengths.

The sensing device 100 may also include memory 330 coupled to the processor 320. In this example, memory 330 includes modules having instructions to configure the processor 320 to perform various operations including to emit light into the cavity 203 (FIG. 2C) of the sensing device 100 and detect light from the cavity 203. For example, in some embodiments, the at least one light source 316 and the at least one sensor 315 may be controlled by the processor 320, for example, with instructions that are stored in memory 330. In this illustrated embodiment, memory 330 may include a sensor component control module 355, which includes a light source control module 335 and a sensor control module 342. The light source control module 335 may include instructions to control one or more of the light sources 316 to emit light and determine how much power to supply to the light source(s) 316 to drive the light emission. The light source control module 335 may also include modulation controls, to control one or more light sources to emit light in a certain sequence, to be activated at certain frequencies and for a certain amount of time. For example, the light source control module 335 may include programs to operate the at least one light source 316. Such programs may be downloaded to the sensing device and stored in the memory 330. The sensor control module 342 can include instructions to operate the at least one sensor, for example to detect radiation at selected wavelengths, and control the at least one sensor to scan a series or range of wavelengths to detect radiation having such wavelengths.

The sensing device 100 may also include a working memory 305 in communication with the processor 305. Working memory 305 may be used by the processor 320 to store a working set of processor instructions contained in the modules of memory 330. Alternatively, working memory 305 may also be used by processor 320 to store dynamic data created during the operation of the sensor component 340.

The sensing device 100 of this example also includes a transceiver (or in some implementations just a transmitter) 327. The transceiver 327 may use a wireless protocol (for example, Bluetooth) to transmit information related to sensed emissions detected by the sensor component 340. In some embodiments, transceiver 327 may be used to download software updates, sensor component programs, data processing programs, comparison programs, information relating to human characteristics that the sensing device is determining (for example blood glucose levels), and/or other instructions for the processor 320.

In some embodiments, the sensing device 100 includes a display. For example, if the sensing device is configured to determine a blood glucose level based on sensed emissions, the determined blood glucose level, whether the result is good or bad, and remedial measures may be shown on the display As described in reference to FIG. 1, in some embodiments the sensing device 100 is configured to collect spectral data and send it to a mobile device (or another computer). In other embodiments the sensing device is configured to process the spectral data to determine if a certain gas or volatile organic compound (VOC) is detected, and then compare the detected matter to human characteristic information. For example, for glucose, processing the spectral information can determine a glucose level in mg/dl, and this glucose level can then be compared to human characteristic information to determine if the glucose level is elevated or normal. In such embodiments, the sensing device 100 includes functionality to process the sensed spectral data, for example, a spectral data processing module 346, and also includes functionality to compare a determined value that results from processing the spectral data to a set of information to identify an amount or level of a detected gas or VOC, for example, in a comparison and identification processing module 350, both of which may be stored in memory 330. The sensing device 100 may also include an additional memory 310 to store additional data or instructions for the sensing device 100.

FIG. 3B is an block diagram illustrating an example of an embodiment of components of a mobile device 125 configured to communicate with a sensing device 100, for example, the sensing device 100 illustrated in FIG. 3A. The mobile device 125 may be any kind of suitable computer, including a cell phone, a smart watch, a laptop, a tablet computer, or a specifically designed computing device that can perform the desired functionality. The illustrated components of the mobile device 125 may perform the same functions as the same named and numbered components as described for the sensing device 100 in reference to FIG. 3A, as in some embodiments the sensing device 100 itself may be configured to perform emission sensing and the subsequent processing for determining what is sensed and what level of a substance has been sensed.

In the illustrated embodiment, the mobile device 125 incudes a processor 320 coupled to working memory 305, a display 325, a transceiver 326, and storage 310. The transceiver 327 is used to receive data including spectral data from the sensing device 100. The processor is also coupled to memory 330 that includes modules having instructions to configure the processor to process spectral data received from the sensing device 100. For example, spectral data processing module 346 can process the received spectral data and generate spatial information. Comparison and identification module 350 can process the spatial information to compare it to known information data sets to determine a level of a substance sensed by the sensing device 100, for example, a blood glucose level. As used herein, "spectral data" is a broad term that refers to output from a detector or sensor component of the sensing device 100. As used herein "spatial information" is a broad term that refers to information that is determined or generated as a result of processing the spectral data. Accordingly, the spatial information corresponds to the spectral data. The two different terms are generally used to distinguish spectral data that is essentially generated from a sensor and information that is determined as a result of processing the spectral data. However, as one skilled in the art would appreciate, when "raw" spectral data is transmitted, the received spectral data may represent the spectral data but be in a different format, accordingly, the received representative spectral data may still be referred to as spectral data. The illustrated components of the mobile device 125 perform the same functions as the same named and numbered components as described for the sensing device 100 in reference to FIG. 3A, as in some embodiments the sensing device 100 itself may be configured to perform emission sensing and the subsequent processing for determining what is sensed and what level of a substance has been sensed.

FIG. 4 is a schematic illustrating a lower portion of a sensing device 100 having two light sources 204 arranged to provide radiation 503 into a collection cavity 203 of the sensing device 100. A sensor 212 detects a spectrum of radiation in the cavity 203 after the radiation emitted from the light sources 204 has propagated through gases and/or VOC's emitted through (or from) skin 501. The sensor 212 can be controlled by a processor 320 (FIG. 3A) in the sensing device 100 to detect the strength of radiation across a plurality of wavelengths to target the detection of a certain substance, such as an indicator of blood glucose level. In various embodiments, sensed spectral data (data/signals output from the detector 212) may be further processed in the sensing device 100, the mobile device 125 (FIG. 1), or the computing device 155 (FIG. 1) to identify a substance detected in the cavity and determine a corresponding amount of a human characteristic (e.g., blood glucose level).

FIGS. 5A and 5B are schematics that illustrate two views of an example of another embodiment of an arrangement of light sources and sensors that may be included in a sensing device 100. The illustrations in FIGS. 5A and 5B show a lower portion of a sensing device 100. In this embodiment, the sensing device includes a first set of light sources 602 and 604 arranged to emit light into cavity 603 via a port 612. In some embodiments, the light sources 602 and 604 may be different, that is, emit different wavelengths, different spectrum of wavelengths, emit a spectrum of wavelengths centered at a different wavelength, emit radiation a different power, and/or be physically different. This embodiment includes two other sets of light sources (that is, a second set of light sources and a third set of light sources) which emit light into the cavity 203 through ports 610 and 614, respectively. The light sources 602 and 604 may be activated separately or at the same time, and can be controlled by processor 320 (FIG. 3A) of the sensing device 100. A second set of light sources 613 and 615 are arranged to emit light into cavity 603 via port 610. A third set of light sources 607 and 605 are arranged to emit light into cavity 603 via port 614. The second and third sets of light sources may operate in the same manner as the first set of light sources.

This embodiment also includes a first set of detectors 606 and 608 that are disposed in proximity to the first set of light sources 602 and 604, and detect radiation in the cavity 203 propagating to the detectors 606 and 608 via port 612. A second set of detectors 617 and 619 are disposed in proximity to the second set of light sources 613 and 615, and detect radiation in the cavity 203 propagating to the detectors 617 and 619 via port 610. A third set of detectors 609 and 611 are disposed in proximity to the third set of light sources 605 and 607, and detect radiation in the cavity 203 propagating to the detectors 609 and 611 via port 614. The detectors 606 and 608 may be alike or different (for example, to detect a different spectral range). In various embodiments, the detectors 606 and 608 can be tuned and controlled to scan through a range of wavelengths to sense a signal at a plurality of wavelengths. The detection of signals across a range of wavelengths can be referred to as spectral data. The second and third sets of detectors can operate in the same manner as the first set of detectors.

The illustrated embodiment may also include one or more auxiliary sensors, for example to sense temperature, oxygen, heart rate, electro-cardio signals and/or environmental conditions. For example, the edge 620 may be configured as a temperature sensor to detect the temperature of a surface it is placed against, and then provide temperature information to the processor 320 of the sensing device 100. The sensing device 100 may also include a temperature sensor for detecting the environmental temperature. The sensing device 100 may further include a motion sensor, such as an accelerometer, to detect body motion. The motion sensor may be able to detect events such as a fall by a user wearing the sensing device 100 or detachment of the sensing device from the user.

The sensor device 100 further includes auxiliary sensor nests 618, 621, 624. Auxiliary sensor nests 618, 621, and 624 are configured to engage one or more auxiliary sensors including, but not limited to, a pulse oximetry sensor, a capnography sensor, a non-invasive blood pressure sensor, an impedance respiration sensor, a ketone detector, a heart rate sensor, an oxygen saturation sensor, a body temperature sensor, an external temperature sensor, a motion sensor, or an electro cardio signal sensor.

FIG. 5C illustrates an example of an embodiment of a detector 600 that may be used to provide calibration information to the sensing device 100. The detector 600 includes a diffuser window 602 positioned in the concave bottom surface 202 of the sensing device 100 providing a port for radiation in the cavity to propagate through towards a filter 604. In some embodiments the diffuser window 602 comprises sapphire, wholly or in part. Filter 604 is configured to allow radiation to pass through towards the sensor 606, such that the radiation that propagates through the filter 604 includes spectral information corresponding to a spectroscopy signature for glucose (for example, an infra-red spectroscopy signature for glucose). In some embodiments, filter 604 comprises multiple layers, and can be, for example, a coated-optic filter.

Sensor 606 is positioned to receive radiation propagating from the cavity 603 that passes through the filter 604, such that the filter 604 is disposed between the diffuser window 602 and the sensor 606. Because of the configuration of the optical filter 604, the sensor 606 generates calibration information for a specific substance (for example, glucose). The sensor 606 is coupled to a processor (for example, processor 320 of FIG. 3B) and provides the calibration data to the processor. The processor can save the calibration data in memory, and use the calibration data to calibrate spectral data received from other detectors that receive radiation from the cavity 603, for example, the first, second and/or third sets of detectors described in reference to FIGS. 5A and 5B.

FIG. 6 is a schematic illustrating an example of data/information flow from a sensing device 100 to a mobile device and display of result, where the sensed data relates to determining a blood glucose level. The sensing device 100 is configured to sense signals in cavity 203 (referring to previous figures) at each wavelengths of a plurality of wavelengths in a spectral range, and generates spectral data. In some embodiments, as illustrated in the embodiment of FIG. 6, the sensing device 100 transmits data 701 to the mobile device 125. In some embodiments, the transmitted data 701 may be information representative of a signal strength across a spectral range 157. In some embodiments, the transmitted data 701 may be information of a detected signal in the frequency domain 153 (for example, when the sensing device 100 includes an interferometer system that is used to sense radiation in the cavity 203). The mobile device 125 receives the transmitted data 701 using transceiver 130. The mobile device 125 includes instructions for the processor 135 to process the spectral data to determine a corresponding level of concentration in blood, and a corresponding glucose level. The processing of the spectral data may be similar to known processing techniques used for IR spectroscopy. The mobile device 125 can include human (or animal) characteristic information 177, stored in a memory component 140. The mobile device 125 is configured to process the spectral data and determine information (spectral information or a value) that can be compared to the stored information and used to determine, for example, a blood concentration and a corresponding glucose level.

FIG. 7 is a flowchart illustrating a process 800 of non-invasively detecting an amount of a substance in a human or an animal, for example, using a sensing device 100 and a mobile device 125 described herein. At block 805 the process 800 emits infra-red light into a cavity of a sensing device, the cavity defined by a concave bottom surface of the sensing device and a surface the sensing device is placed against. This can be performed by a light source 204 as illustrated in FIG. 2C. At block 810 the process 800 generates, with a sensor, spectral data from sensed radiation in the cavity, the spectral data including signals across a plurality of wavelengths and representative of a substance in the cavity, the sensor disposed in a housing of the sensor device to receive radiation from the cavity. At block 815 the process 800 receives at a processor spectral data from the sensor component. At block 820 the process 800 generates, using the processor, spectral information based on the spectral data, the spectral absorption information corresponding to a blood glucose level. At block 825 the process 800 compares the spectral information to data indicative of blood glucose levels stored in a memory component, and determining a blood glucose level indicative of the spectral absorption information.

In some embodiments, the process 800 further includes transmitting the spectral information from a sensing device to a mobile device. In such embodiments, the process 800 may also include comparing the spectral information to data indicative of blood glucose levels is performed by a processor coupled to the memory component, the mobile device comprising the processor and the memory component. The process 800 may also include receiving the spectral information on the mobile device and displaying information representative of the blood glucose level on a display of the mobile device.

FIGS. 8-12 depict an illustrative example of one embodiment of a sensing device 900. FIG. 8 is an exploded perspective view of an illustrative example of one embodiment of a sensing device 900. The sensing device 900 includes a lower housing 2, a beam support frame 4, a micro chamber 3, a battery supply 17, a power supply voltage regulation PCA 10, a central processing unit PCA 11, a communications PCA 12, a radio TX/RX 16, an O-ring 5, an upper housing 3, and a plurality of fasteners 18. FIG. 9 is a sectional view showing taken along line A shown in FIG. 8 of an illustrative example of one embodiment of the sensing device 900. The sensing device 900 includes a dichroic filter mirror component 6, a primary beam receptor 22A, a primary LED/laser source 7A, a reference LED/laser source 7B, and a reference beam receptor 22B.

FIG. 10 is an exploded perspective view of an illustrative example of one embodiment of the sensing device 900 taken from a different side than that shown in FIG. 8.

FIG. 11 is a sectional view taken along line B shown in FIG. 10 of an illustrative example of one embodiment of the sensing device 900.

The lower housing 2 includes a top surface 46 and a bottom surface 44 configured such that when the bottom surface 44 is place against a surface (for example, a skin surface), a chamber or cavity is defined between the bottom surface 44 and the surface that the sensing device 900 is placed against. The lower housing is further configured to receive and secure one or more components of the sensing device 900.

The beam support frame 4 is configured to fit within the interior of the lower housing 2 and includes is bottom surface 48 and a top surface 50. The beam support frame 4 includes support structures 78A-C, each support structure being configured to secure a set of light sources, such as primary LED/laser source 7A and reference LED/laser source 7B, and a set of detectors, such primary beam receptor 22A and reference beam receptor 22B, the detectors being configured to detect radiation. The beam support frame 4 also includes auxiliary sensors nests 80A-C on the external surface of the beam support frame 4 configured to engage one or more auxiliary sensors such as, for example, a pulse oximetry sensor, a capnography sensor, a non-invasive blood pressure sensor, an impedance respiration sensor, a ketone detector, a heart rate sensor, an oxygen saturation sensor, a body temperature sensor, an external temperature sensor, a motion sensor, or an electro cardio signal sensor.

The micro chamber 1 includes a bottom surface 52 and a top surface 54. The micro chamber 1 is configured to fit within the interior of the beam support frame 4. The micro chamber 1 includes ports 30A-C, each port configured to align with a support structure 78A-C supporting a set of light sources and a set of detectors. The ports may further include one or more filters, such as dichroic filter mirror component 6. Dichroic filter mirror component 6 is configured to selectively allow some wavelengths of light to pass while reflecting other wavelengths. For example, the dichroic filter mirror component 6 may filter radiation such that the radiation that propagates through the dichroic filter mirror component 6 includes spectral information corresponding to a spectroscopy signature for glucose (for example, an infrared spectroscopy signature for glucose). The micro chamber 1 further includes a top surface such that, when the micro chamber 1 is positioned within the beam support frame 4 and the beam support frame 4 is positioned within the lower housing 2, a cavity is formed in which each set of light sources can emit light through ports 30A-C and into the cavity and each set of detectors can detect radiation in the cavity propagating through the ports 30A-C, the cavity being defined by the interior walls and the interior of the top surface of the micro chamber 1, as well as a surface upon bottom surface 44 of the lower housing 2 is placed. The micro chamber 1 further includes receiving members 32M-O for receiving the fasteners 18. The receiving members 32M-O are positioned on the top surface 54 of the micro chamber 1 and protrude upward in a direction opposite of the bottom surface 44 of the lower housing 2.

The power supply voltage regulation 10 includes a bottom surface 56 and a top surface 58, where the bottom surface is configured to rest on the top surfaces of the receiving members 32M-O. The battery supply 17 is configured to fit between the top surface 54 of the micro chamber 1 and the bottom surface 56 of the power supply voltage regulation PCA 10. The battery supply 17 engages with and supplies power to the power supply voltage regulation 10. The power supply voltage regulation 10 receives power from the battery supply 17 and provides power to the other components of the sensing device 900. The power supply voltage regulation 10 further includes panels 75A-C that extend distally from the bottom surface 56 of the power supply voltage regulation 10 towards the bottom surface 44 of the lower housing 2 and between the exterior surface of the beam support frame 4 and the interior surface of the lower housing 2. Each panel 75A-C is configured to align with one of the support structures 78A-C and to provide power to each set of lights and set of detectors. The power supply voltage regulation 10 further includes receiving members 32J-L for receiving the fasteners 18. The receiving members 32J-L are positioned on the top surface 58 of the power supply voltage regulation 10 in alignment with the receiving members 32M-O and protrude upward in a direction opposite of the bottom surface 44 of the lower housing 2.

The central processing unit PCA 11 includes a bottom surface 60 and a top surface 62, where the bottom surface is configured to rest on the top surfaces of the receiving members 32J-L. The central processing unit PCA 11 can communicate with the light sources, the detectors, the power supply voltage regulation PCA 10, the communications PCA 12, and the Radio TX/RX 16. The central processing unit PCA 11 may include a memory including modules having instructions to configure the central processing unit PCA 11 to perform various operations including to emit light into the cavity of the sensing device 900 and to detect light from the cavity. For example, in some embodiments, the one or more light sources and one or more detects may be controlled by the central processing unit PCA 11, for example, with instructions that are stored in the memory. In this illustrated embodiment, the memory may include a detector component control module, which includes a light source control module and a detector control module. The light source control module may include instructions to control one or more of the light sources to emit light and determine how much power to supply to the light source(s) to drive the light emission. The light source control module may also include modulation controls, to control one or more light sources to emit light in a certain sequence, to be activated at certain frequencies and for a certain amount of time. Such programs may be downloaded to the sensing device 900 and stored in the memory. The detector control module can include instructions to operate the one or more detectors, for example to detect radiation at selected wavelengths, and control the one or more detectors to scan a series or range of wavelengths to detect radiation having such wavelengths.

The central processing unit PCA 11 can be configured to process spectral data received from the one or more detectors, such as for example, spectral data to determine if a certain gas or volatile organic compound (VOC) is detected, and then compare the detected matter to human characteristic information. For example, for glucose, processing the spectral information can determine a glucose level in mg/dl, and this glucose level can then be compared to human characteristic information to determine if the glucose level is elevated or normal. Human characteristic information may be stored in the memory of the sensing device 900 or received from an external device. In such embodiments, the central processing unit 11 includes functionality to process the sensed spectral data, for example, a spectral data processing module, and also includes functionality to compare a determined value that results from processing the spectral data to a set of information to identify an amount or level of a detected gas or VOC, for example, in a comparison and identification processing module, both of which may be stored in memory. The sensing device 900 may also include an additional memory to store additional data or instructions for the sensing device 900.

The central processing unit PCA 11 further includes receiving members 32G-I for receiving fasteners 18. The receiving members 32G-I are positioned on the top surface 62 of the central processing unit PCA 11 in alignment with the receiving members 32J-L and protrude upward in a direction opposite of the bottom surface 44 of the lower housing 2.

The communications PCA 12 includes a bottom surface 64 and a top surface 66, where the bottom surface is configured to rest on the top surfaces of the receiving members 32G-I. The communications PCA 12 receives power from the power supply voltage regulation PCA 10 and is in communication with the central processing unit PCA 11. Mounted on the top surface of the communications PCA 12 is the radio TX/RX 16. The radio TX/RX is configured to transmit data to and receive data from one or more external devices, such as, for example, mobile device 125 and computing device 155 described above. The radio TX/RX 16 may communicate through a wireless protocol (e.g., Bluetooth). In some embodiments, the sensing device may further be configured to communicate through wired protocols (e.g., USB interface). The communications PCA 12 further includes a pair of Bluetooth LEDs 74A,B. The central processing unit PCA 11 can be configured to activate the Bluetooth LED 74A,B when the Bluetooth wireless protocol is in use. The communications PCA 12 further includes the power button 36. Power button 36 can be in communication with the central processing unit PCA 11 and the power supply voltage regulation PCA 10. When engaged, the power button 36 can communicate with the processor such that the processor supplies power to the sensing device 900 or cease's the supply of power to the sensing device 900. The power button 36 may further include an LED for indicating the power state of the device. The power button 36 may display different colors and/or emit light at particular intervals to indicate the power state of the sensing device 900. Some examples of power states include on, off, charged, charging, out of power, or needs to be charged. The communications PCA 12 further includes receiving holes 32D-F aligned with receiving members 32G-I for receiving fasteners 18.

The upper housing 3 includes a bottom surface 68 and a top surface 70. The bottom surface 68 is configured to rest on the top surface 66 of the communications PCA 12 and the top surface 46 of the lower housing 2. The beam support frame 4, micro chamber 1, battery supply 17, power supply voltage regulation PCA 10, central processing unit PCA 11, communications PCA 12, and radio TX/RX 16 are configured to fit within the lower housing 2. The O-ring 3 can be positioned to create a seal between the top surface 46 of the lower housing 2 and a bottom surface 68 of the upper housing 3. The upper housing 3 further includes receiving holes 32A-C aligned with receiving holes 32D-F for receiving fasteners 18. The fasteners 18, when inserted into receiving holes 32A-O secure the micro chamber 1, power supply voltage regulation PCA 10, central processing unit PCA 11, communications PCA 12, and upper housing 3 in place. The top surface 70 of the upper housing 3 further includes an opening 34 from which the power button 36 protrudes allowing for external engagement of the power button 36 and visibility of the LED of power button 36. The opening 34 allows for the visibility of the LED of power 36 when top surface 70 of the upper housing 3 is visible. The upper housing 3 further includes a vent 38 positioned above the radio TX/RX 16. The upper housing 3 also includes a set of openings 42A, B through which Bluetooth LEDs 74A, B protrude. The openings 42A, B allow for visibility of the Bluetooth LEDs 74A,B when the top surface 70 of the upper housing is visible. FIG. 12 shows a cross-sectional view of an illustrative example of one embodiment of a sensing device 900. FIG. 12 shows a reference beam receptor 22C and the reference LED/laser source 7C positioned within the port 30C. FIG. 12 further depicts a concave inner surface 40 of the micro chamber 1. The concave inner surface 40 creates a cavity when the bottom surface 44 of the lower housing 2 is positioned against a surface such as a skin surface, such that one or more of the sets of detectors can detect radiation from light propagating from the one or more sets of light sources through the cavity and through emissions from the skin.

Additional disclosure of certain embodiments of a sensing device are included in the appendix filed herewith, which is a part of this provisional application. The various illustrative methods, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions and processes described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method, algorithm or manufacturing process disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blue-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. To the extent that the word "exemplary" is used herein, it exclusively means "serving as an example, instance, or illustration." Any implementation described herein as "exemplary" is not necessarily to be construed as preferred or advantageous over other possibilities or implementations. Additionally, a person having ordinary skill in the art will readily appreciate, the any relative term used or indicated herein, for example, "upper" and "lower," are sometimes used for ease of describing the figures, and indicate relative positions corresponding to the orientation of the figure on a properly oriented page, and may not reflect the proper orientation of an IMOD as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, a person having ordinary skill in the art will readily recognize that such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

What is claimed is:

1. A system for detecting emissions through skin, comprising:
    a sensing device comprising
    a housing having a top portion and a bottom portion, the bottom portion having a concave-shaped bottom surface creating a cavity region;
        at least one infrared light source disposed in a portion of the bottom portion, the at least one infrared light source arranged to emit a spectral range of wavelengths of light into the cavity region;
        at least one sensor, including a spectrometer, disposed to receive and detect light emitted by the at least one infrared light source after the light propagates through at least a portion of the cavity region, the at least one sensor configured to generate a signal based on received light;
        a processor coupled to the sensor being operable to receive spectral absorption data from the at least one sensor, and determine spectral information, using absorption spectroscopy, based on the received spectral absorption data, the spectral information being representative of the absorption of light by gases in the cavity region; and
        a communication module coupled to the processor, the communication module configured to receive the spectral information from the processor and to wirelessly transmit the spectral information.

2. The system of claim 1, further comprising a mobile device comprising:
    a transceiver configured to receive a communication that includes the information representative of the signal;
    a memory component configured to store data indicative of blood glucose levels corresponding to the spectral information; and
    a processor coupled to the transceiver and the memory component, the processor configured to receive the spectral information, compare the spectral information to the data indicative of the blood glucose levels, and determine a blood glucose level corresponding to the spectral information.

3. The system of claim 2, wherein the sensing device further comprises a display, and wherein the processor is further configured to provide information representative of the glucose level on the display.

4. The system of claim 2, wherein the memory includes predetermined data that includes spectral information and blood glucose levels that correspond to the spectral information.

5. The system of claim 1, wherein the sensing device further comprises
a memory component configured to store data indicative of blood glucose levels corresponding to the spectral absorption information, and
wherein the processor is configured to compare the spectral information to the data indicative of blood glucose levels and determine a blood glucose level corresponding to received spectral data.

6. The system of claim 5, wherein the sensing device further comprises a display, and wherein the processor is further configured to provide information representative of the glucose level on the display.

7. The system of claim 5, wherein the processor is further configured to communicate information representative of the blood glucose level to a remote computer via a network that is at least partially wireless.

8. The system of claim 1, wherein the sensing device further comprises at least one of a heart rate sensor, an oxygen saturation sensor, a temperature sensor, or an electro cardio signal sensor.

9. The system of claim 1, wherein the at least one light source comprises two or more light sources, and wherein spectral information is based on light received from the two or more light sources.

10. The system of claim 1, wherein the spectrometer comprises a Fourier transform infrared spectroscopy (FTIR) spectrometer.

11. The system of claim 1, wherein the communication module is further configured to wirelessly transmit the spectral absorption information to an insulin delivery device.

12. A system for detecting emissions through skin, comprising:
a sensing device comprising
a collection cavity;
a Fourier transform infrared spectroscopy (FTIR) spectrometer configured to generate spectral data representative of how gas in the collection cavity absorbs infra-red light at a plurality of wavelengths; and
a processor coupled to the FTIR spectrometer and configured to receive the spectral data from the FTIR spectrometer, the processor further configured to generate spectral information based on the spectral data, the spectral information corresponding to a blood glucose level.

13. The system of claim 12, wherein the sensing device further comprises a communication module coupled to the processor, the communication module configured to receive the spectral information from the processor and to wirelessly transmit the spectral information, and
wherein the system further comprises
a mobile device comprising
a transceiver configured to receive a communication that includes the spectral information;
a memory component configured to store data indicative of blood glucose levels corresponding to the spectral information, and
a processor coupled to the transceiver and the memory component, the processor configured to receive the spectral information, compare the spectral information to the data indicative of blood glucose levels stored in the memory component, and determine a blood glucose level indicative of the spectral information.

14. The system of claim 12, wherein the sensing device further comprises
a memory component configured to store data indicative of blood glucose levels corresponding to the spectral information; and
wherein the processor is coupled to the memory component, the processor further configured to receive the spectral information, compare the spectral information to the data indicative of blood glucose levels stored in the memory component, and determine a blood glucose level indicative of the spectral information.

15. A method of determining a blood glucose level from gas emitted from skin, the method comprising:
emitting infra-red light into a cavity of a sensing device, the cavity defined by a concave bottom surface of the sensing device and a surface the sensing device is placed against;
generating, with a sensor, spectral data from sensed radiation, representative of absorbed spectra, in the cavity, the spectral data including signals across a plurality of wavelengths and representative of a substance in the cavity, the sensor disposed in a housing of the sensor device to receive radiation from the cavity;
receiving at a processor spectral data from the sensor component;
generating, using the processor; spectral information based on the spectral data, the spectral absorption information corresponding to a blood glucose level; and
comparing the spectral absorption information to data indicative of blood glucose levels stored in a memory component, and determining a blood glucose level indicative of the spectral absorption information.

16. The method of claim 15, further comprising transmitting the spectral absorption information from a sensing device to a mobile device.

17. The method of claim 16, wherein comparing the the spectral absorption information to data indicative of blood glucose levels is performed by a processor coupled to the memory component, the mobile device comprising the processor and the memory component.

18. The method of claim 16, further comprising receiving the spectral absorption information on the mobile device; and displaying information representative of the blood glucose level on a display of the mobile device.

* * * * *